(12) United States Patent
Ootsuki et al.

(10) Patent No.: US 10,716,471 B2
(45) Date of Patent: Jul. 21, 2020

(54) CONTROL DEVICE, CONTROL METHOD, AND MICROSCOPE DEVICE FOR OPERATION

(71) Applicant: SONY CORPORATION, Tokyo (JP)

(72) Inventors: Tomoyuki Ootsuki, Kanagawa (JP); Atsushi Miyamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 21 days.

(21) Appl. No.: 15/845,431

(22) Filed: Dec. 18, 2017

(65) Prior Publication Data

US 2018/0104018 A1    Apr. 19, 2018

Related U.S. Application Data

(63) Continuation of application No. 15/556,367, filed as application No. PCT/JP2017/004385 on Feb. 7, 2017, now Pat. No. 10,595,955.

(30) Foreign Application Priority Data

Mar. 30, 2016    (JP) .................................. 2016-067323

(51) Int. Cl.
   *A61B 3/00*    (2006.01)
   *A61B 3/13*    (2006.01)
   (Continued)

(52) U.S. Cl.
   CPC ................. *A61B 3/13* (2013.01); *A61B 3/00* (2013.01); *A61B 3/0075* (2013.01); *A61B 3/08* (2013.01);
   (Continued)

(58) Field of Classification Search
   CPC ......... A61B 3/0075; A61B 3/13; A61B 90/20; A61B 90/25; A61B 3/0016; A61B 3/14;
   (Continued)

(56) References Cited

U.S. PATENT DOCUMENTS 6,175,642 B1    1/2001 Gobbi et al.
2011/0304819 A1    12/2011 Juhasz et al.
(Continued)

FOREIGN PATENT DOCUMENTS

CN    103815972 A    5/2014
CN    103860270 A    6/2014
(Continued)

OTHER PUBLICATIONS

Combined Chinese Office Action and Search Report dated Dec. 11, 2018 in Patent Application No. 201780000978.X (with English translation).
(Continued)

*Primary Examiner* — Jordan M Schwartz
(74) *Attorney, Agent, or Firm* — Xsensus LLP

(57) ABSTRACT

To make it possible to improve user convenience, provided is a control device including: a control unit configured to control a position and an attitude of a microscope unit by driving an arm unit that supports the microscope unit on the basis of a captured image of an operating site photographed by the microscope unit during an operation so that a position and attitude condition set before the operation is satisfied. The position and attitude condition is a condition that prescribes a position and an attitude of the microscope unit with respect to the operating site to obtain a desired captured image corresponding to the position and attitude condition.

27 Claims, 16 Drawing Sheets

(51) Int. Cl.

| | |
|---|---|
| *A61B 3/14* | (2006.01) |
| *A61B 90/20* | (2016.01) |
| *A61B 90/25* | (2016.01) |
| *G02B 21/36* | (2006.01) |
| *G02B 21/24* | (2006.01) |
| *G05D 3/00* | (2006.01) |
| *B25J 13/08* | (2006.01) |
| *A61B 34/10* | (2016.01) |
| *A61B 46/00* | (2016.01) |
| *A61B 46/20* | (2016.01) |
| *A61F 9/007* | (2006.01) |
| *A61B 3/08* | (2006.01) |
| *G05D 3/20* | (2006.01) |
| *A61B 34/00* | (2016.01) |
| *G06K 9/00* | (2006.01) |
| *G06T 7/00* | (2017.01) |
| *H04N 5/232* | (2006.01) |
| *A61B 34/20* | (2016.01) |
| *A61B 17/02* | (2006.01) |
| *A61B 90/00* | (2016.01) |
| *A61B 90/30* | (2016.01) |

(52) U.S. Cl.
CPC ............... *A61B 3/14* (2013.01); *A61B 34/10* (2016.02); *A61B 34/25* (2016.02); *A61B 46/00* (2016.02); *A61B 46/20* (2016.02); *A61B 90/20* (2016.02); *A61B 90/25* (2016.02); *A61F 9/007* (2013.01); *B25J 13/08* (2013.01); *G02B 21/24* (2013.01); *G02B 21/36* (2013.01); *G02B 21/367* (2013.01); *G05D 3/00* (2013.01); *G05D 3/20* (2013.01); *G06K 9/00604* (2013.01); *G06T 7/0016* (2013.01); *H04N 5/23212* (2013.01); *A61B 3/145* (2013.01); *A61B 17/0231* (2013.01); *A61B 2034/2059* (2016.02); *A61B 2034/2065* (2016.02); *A61B 2090/309* (2016.02); *A61B 2090/3954* (2016.02); *G06T 2207/10056* (2013.01); *G06T 2207/30041* (2013.01)

(58) Field of Classification Search
CPC ........... A61B 3/145; A61B 3/10; A61B 34/25; G02B 21/365; G02B 21/367; G06T 7/0016; G06T 2207/10056; G06T 2207/30041
See application file for complete search history.

(56) References Cited

U.S. PATENT DOCUMENTS

| | | | |
|---|---|---|---|
| 2012/0190967 A1* | 7/2012 | Nahm | A61B 6/504 600/411 |
| 2012/0320186 A1* | 12/2012 | Urban | A61B 34/30 348/79 |
| 2013/0050645 A1 | 2/2013 | Sato et al. | |
| 2015/0250547 A1 | 9/2015 | Fukushima et al. | |
| 2015/0313679 A1 | 11/2015 | Fukushima et al. | |
| 2016/0220324 A1* | 8/2016 | Tesar | G02B 21/0012 |
| 2017/0079729 A1 | 3/2017 | Fukushima et al. | |
| 2017/0143429 A1 | 5/2017 | Richmond et al. | |
| 2017/0143442 A1* | 5/2017 | Tesar | A61B 90/37 |
| 2018/0055356 A1 | 3/2018 | Shibata et al. | |
| 2018/0110571 A1* | 4/2018 | Hallen | A61B 34/74 |
| 2018/0256008 A1* | 9/2018 | Nishizawa | A61B 34/20 |

FOREIGN PATENT DOCUMENTS

| | | |
|---|---|---|
| EP | 0 740 179 A1 | 10/1996 |
| JP | 06-003597 A | 1/1994 |
| JP | 2012-138219 A | 7/2012 |
| JP | 2015-192697 A | 11/2017 |
| WO | 2015/151447 A1 | 10/2015 |

OTHER PUBLICATIONS

Combined Office Action and Search Report dated Jun. 14, 2018 in Chinese Patent Application No. 201780000978.X (with English language translation), 13 pages.
Extended European Search Report dated Jun. 25, 2018 in Patent Application No. 17755408.6, 9 pages.
Written Opinion of the International Searching Authority issued in International Application No. PCT/JP2017/004335 dated Mar. 21, 2017.

* cited by examiner

FIG. 4

| | | |
|---|---|---|
| Dr.AAA: UPWARD INCISION | Dr.DDD: UPWARD INCISION | Dr.GGG: UPWARD INCISION |
| Dr.AAA: INCISION OF LEFT EYE TO EAR SIDE | Dr.DDD: INCISION OF LEFT EYE TO EAR SIDE | Dr.GGG: INCISION OF LEFT EYE TO EAR SIDE |
| Dr.AAA: INCISION OF RIGHT EYE TO EAR SIDE | Dr.DDD: INCISION OF RIGHT EYE TO EAR SIDE | Dr.GGG: INCISION OF RIGHT EYE TO EAR SIDE |
| Dr.BBB: UPWARD INCISION | Dr.EEE: UPWARD INCISION | Dr.HHH: UPWARD INCISION |
| Dr.BBB: INCISION OF LEFT EYE TO EAR SIDE | Dr.EEE: INCISION OF LEFT EYE TO EAR SIDE | Dr.HHH: INCISION OF LEFT EYE TO EAR SIDE |
| Dr.BBB: INCISION OF RIGHT EYE TO EAR SIDE | Dr.EEE: INCISION OF RIGHT EYE TO EAR SIDE | Dr.HHH: INCISION OF RIGHT EYE TO EAR SIDE |
| Dr.CCC UPWARD INCISION | Dr.FFF: UPWARD INCISION | Dr.JJJ: UPWARD INCISION |
| Dr.CCC: INCISION OF LEFT EYE TO EAR SIDE | Dr.FFF: INCISION OF LEFT EYE TO EAR SIDE | |
| Dr.CCC: INCISION OF RIGHT EYE TO EAR SIDE | Dr.FFF: INCISION OF RIGHT EYE TO EAR SIDE | |

CONTROL DEVICE, CONTROL METHOD, AND MICROSCOPE DEVICE FOR OPERATION

CROSS REFERENCE TO RELATED APPLICATIONS

This application is a continuation of U.S. application Ser. No. 15/556,367, filed Sep. 7, 2017, which is a National Stage of PCT/JP2017/004385 filed Feb. 7, 2017, which claims the benefit of priority from Japanese Patent Application No. 2016-067323, filed Mar. 30, 2016, the contents of each which is incorporated herewith by reference in its entirety.

TECHNICAL FIELD

The present disclosure relates to a control device, a control method, and a microscope device for operation.

BACKGROUND ART

Microscope devices have been used in surgical operations. A microscope device is configured such that an arm unit supports an electronic imaging microscope unit (a video microscope unit). An operator performs a surgical operation viewing an enlarged operating site using a video photographed by the microscope unit.

With respect to such microscope devices, there have been demands for control of positions and attitudes of microscope units thereof with high precision to obtain desired videos. In particular, in a case in which photographing at a high magnification factor is being performed, a slight deviation of a position and an attitude of a microscope unit leads to a significant deviation of a video, and thus a position and an attitude of the microscope unit are required to be controlled with high precision. A user normally moves a position and an attitude of such a microscope unit using his or her hand; however, when highly precise positioning is performed with his or her hand, the user has to do delicate work, which increases a burden of the user and causes the positioning work prolonged, and even leads to a lengthened operation time.

Here, Patent Literature 1 discloses a technology relating to a scanning electron microscope, rather than such a microscope device for operation described above, for reducing a burden of manipulation of a user to obtain a desired image. Specifically, a stage on which a sample is placed is automatically moved so that a desired image designated by a user is obtained in the technology disclosed in Patent Literature 1. According to this technology, a desired image can be automatically obtained only by performing a user's simple manipulation of designating the desired image, and thus a burden of the user can be reduced.

CITATION LIST

Patent Literature

Patent Literature 1: JP 2012-138219A

DISCLOSURE OF INVENTION

Technical Problem

Taking account of the above-described circumstance, a technology with respect to a microscope device for operation that reduces a burden of manipulation of a user with respect to acquisition of a desired image and improves user convenience as disclosed in Patent Literature 1 has been demanded.

Therefore, the present disclosure proposes a novel and improved control device, control method, and microscope device for operation which can improve user convenience.

Solution to Problem

According to the present disclosure, there is provided a control device including: a control unit configured to control a position and an attitude of a microscope unit by driving an arm unit that supports the microscope unit on the basis of a captured image of an operating site photographed by the microscope unit during an operation so that a position and attitude condition set before the operation is satisfied. The position and attitude condition is a condition that prescribes a position and an attitude of the microscope unit with respect to the operating site to obtain a desired captured image corresponding to the position and attitude condition.

In addition, according to the present disclosure, there is provided a control method including: controlling, by a processor, a position and an attitude of a microscope unit by driving an arm unit that supports the microscope unit on the basis of a captured image of an operating site photographed by the microscope unit during an operation so that a position and attitude condition set before the operation is satisfied. The position and attitude condition is a condition that prescribes a position and an attitude of the microscope unit with respect to the operating site to obtain a desired captured image corresponding to the position and attitude condition.

In addition, according to the present disclosure, there is provided A microscope device for operation including: a microscope unit configured to photograph a captured image of an operating site; an arm unit configured to support the microscope unit; and a control device configured to control a position and an attitude of the microscope unit by driving the arm unit on the basis of a captured image of the operating site photographed by the microscope unit during an operation so that a position and attitude condition set before the operation is satisfied. The position and attitude condition is a condition that prescribes a position and an attitude of the microscope unit with respect to the operating site to obtain a desired captured image corresponding to the position and attitude condition.

According to the present disclosure, a position and an attitude of a microscope unit are controlled so that a position and an attitude condition for obtaining a desired captured image set before an operation is satisfied on the basis of a captured image of an operating site photographed by the microscope unit during the operation. Thus, the microscope unit can be automatically moved to a position and an attitude at which the desired captured image is obtained without a complicated manipulation of a user. Therefore, a burden of the user can be reduced and user convenience can be improved.

Advantageous Effects of Invention

According to the present disclosure described above, user convenience can be enhanced. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 4 is a diagram illustrating an example of a GUI on which position and attitude conditions are designated.

MODE(S) FOR CARRYING OUT THE INVENTION

Figure 1:
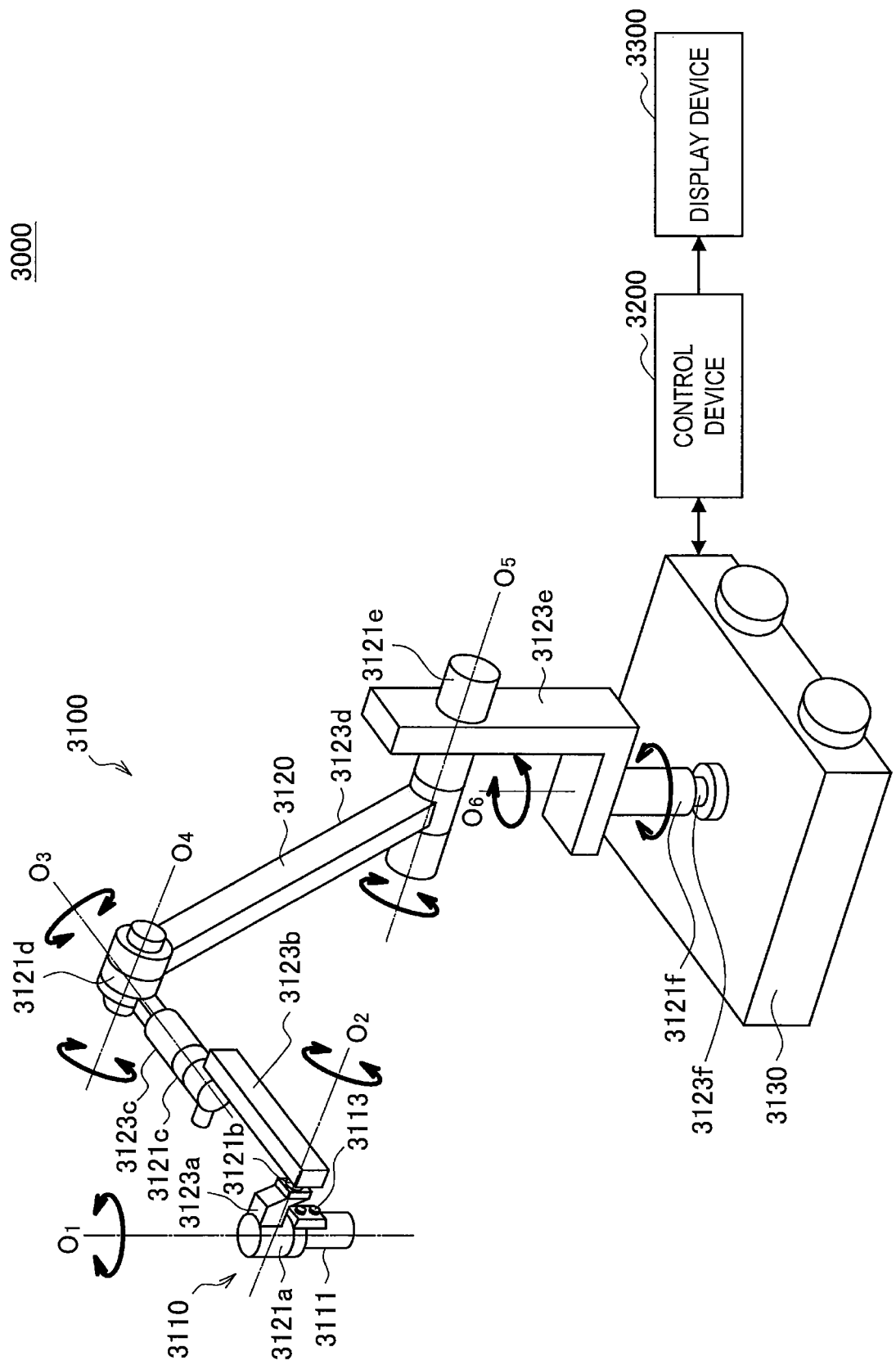
FIG. 1 is a diagram illustrating an example of a schematic configuration of a microscopic operation system according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.
1. First embodiment
1-1. Configuration of microscopic operation system
1-2. Configuration of drive control system
1-3. Processing sequence of control method
2. Second embodiment
2-1. Configuration of drive control system
2-2. Processing sequence of control method
3. Modified examples
3-1. Updating of position and attitude condition through learning
3-2. Other example of instruction included in position and attitude condition
3-3. Other example of registration method of instruction regarding appearance of image
3-4. Other example of designation method for position and attitude condition
3-5. Restriction on movement of microscope unit
4. Supplement Note that, in the present specification, a "user" is assumed to mean at least one of medical staff members (a doctor (an operator) who gives treatment on an operating site, an assistant, or the like) who use a microscopic operation system and/or a drive control system which will be described below. The "user" is described as an operator, an assistant, or the like particularly when he or she needs to be distinguished.

In addition, examples in which the technology according to the present disclosure is applied to an ophthalmic surgery will be described below. However, the present disclosure is not limited thereto and the technology according to the present disclosure may be applied to various types of operations that can be performed using the microscopic operation system that will be described below, for example, brain surgeries, and the like.

1. First Embodiment (1-1. Configuration of Microscopic Operation System)

A configuration of a microscopic operation system according to a first embodiment of the present disclosure will be described with reference to FIG. 1. FIG. 1 is a diagram illustrating an example of a schematic configuration of the microscopic operation system according to the first embodiment. Referring to FIG. 1, the microscopic operation system 3000 is constituted by a microscope device 3100, a control device 3200, and a display device 3300.

The microscope device 3100 has a microscope unit 3110 for enlarging and observing an observation object (an eye of a patient that is an operating site), an arm unit 3120 that supports the microscope unit 3110 at its leading end, and a base unit 3130 that supports a base end of the arm unit 3120.

The microscope unit 3110 is made up of an approximately cylindrical barrel unit 3111, an imaging unit (not illustrated) provided inside the barrel unit 3111, and an operating unit 3113 provided in a partial region on the outer circumference of the barrel unit 3111. The microscope unit 3110 is an electronic imaging microscope unit (a video microscope unit) that images a captured image electronically with the imaging unit.

The aperture on the bottom end of the barrel unit 3111 is provided with a cover glass that protects the imaging unit inside. Light from an observation target (hereinafter also called observation light) passes through the cover glass and is incident on the imaging unit inside the barrel unit 3111. Note that a light source made up of a light-emitting diode (LED) or the like, for example, may also be provided inside the barrel unit 3111, and during imaging, light may be radiated from the light source onto the observation target through the cover glass.

The imaging unit is made up of an optical system that condenses observation light, and an image sensor that senses the observation light condensed by the optical system. The optical system is made up of a combination of multiple lenses, including a zoom lens and a focus lens, the optical characteristics of which are adjusted so that an image of the observation light is formed on the light-sensitive face of the image sensor. The image sensor senses and photoelectrically converts the observation light to thereby generate a signal corresponding to the observation light, or in other words, an image signal corresponding to the observed image. A sensor capable of color photography including a Bayer array, for example, is used as the image sensor. The image sensor may be any of various known types of image sensors, such as a complementary metal-oxide-semiconductor (CMOS) image sensor or a charge-coupled device (CCD) image sensor. The image signal generated by the image sensor is transmitted to the control device 3200 as raw data. At this point, the transmission of the image signal may be conducted favorably by optical communication. This is because at the surgery venue, an operator performs a operation while observing the state of a lesion via the captured image, and thus for safer and more reliable surgery, there is demand for the moving image of an eye that is the operating site to be displayed as close to real-time as possible. Transmitting the image signal by optical communication makes it possible to display the captured image without delay.

Note that the imaging unit also includes a drive mechanism that moves the zoom lens and the focus lens of the optical system along the optical axis. By suitably moving the zoom lens and the focus lens with the drive mechanism, the magnification factor of the captured image and the focus distance during imaging may be adjusted. Also, the imaging unit may be provided with any of various types of functions typically provided in electronic imaging microscope units, such as an auto exposure (AE) function, an auto focus (AF) function or the like.

In addition, the imaging unit may be configured as a so-called one-chip imaging unit that includes a single image sensor, or as a so-called multi-chip imaging unit that includes multiple image sensors. If the imaging unit has a multi-chip configuration, image signals corresponding to R, G, and B are generated by respective image sensors, for example, and a color image may be obtained by combining these image signals. Alternatively, the imaging unit may be configured to include a pair of image sensors for respectively acquiring image signals for the right eye and the left eye corresponding to stereoscopic vision (3D display). By presenting 3D display, the operator is able to grasp the depth of the operating site more accurately. Note that if the imaging unit has a multi-chip configuration, the optical system is provided with multiple subsystems corresponding to each of the image sensors.

The operating unit 3113 is made up of elements such as a directional lever or switches, for example, and is an input unit that accepts operating input from a user. For example, via the operating unit 3113, the user is able to input an instruction to change the magnification factor of the observation target and the focus distance (focus). By having the drive mechanism of the imaging unit suitably drive the zoom lens and the focus lens in accordance with the instruction, the magnification factor and the focus may be adjusted. As another example, via the operating unit 3113, the user is able to input an instruction to toggle the operating mode of the arm unit 3120 (a free mode and a locked mode that will be described later). Note that when the user wants to move the microscope unit 3110, it is anticipated that the user moves the microscope unit 3110 while switching the operating mode of the arm unit 3120 to the free mode by gripping and holding the barrel unit 3111. Consequently, the operating unit 3113 preferably is provided at a position that allows easy operation with the fingers while the user is gripping the barrel unit 3111, to thereby allow the user to operate the operating unit 3113 even while moving the barrel unit 3111.

The arm unit 3120 is configured as a result of multiple links (a first link 3123a to a sixth link 3123f) being rotatably joined to each other by multiple joint units (a first joint unit 3121a to a sixth joint unit 3121f).

The first joint unit 3121a has an approximately cylindrical shape, and on the leading end (bottom end) thereof supports the top end of the barrel unit 3111 of the microscope unit 3110, so as to allow rotation about a rotation axis (first axis $O_1$) parallel to the central axis of the barrel unit 3111. Herein, the first joint unit 3121a may be configured so that the first axis $O_1$ is aligned with the optical axis of the microscope unit 3110. Consequently, rotating the microscope unit 3110 about the first axis $O_1$ makes it possible to change the field of view as though rotating the captured image.

The first link 3123a securely supports the first joint unit 3121a on the leading end thereof. Specifically, the first link 3123a is an approximately L-shaped rod-like member, the leading edge of which extends in a direction orthogonal to the first axis $O_1$, while also being connected to the first joint unit 3121a so that the end of that edge abuts the top end on the outer circumference of the first joint unit 3121a. The second joint unit 3121b is connected to the end of the base edge of the approximate L-shape of the first link 3123a.

The second joint unit 3121b has an approximately cylindrical shape, and on the leading end thereof supports the base end of the first link 3123a, so as to allow rotation about a rotation axis (second axis $O_2$) orthogonal to the first axis $O_1$. The leading end of the second link 3123b is securely connected to the base end of the second joint unit 3121b.

The second link 3123b is an approximately L-shaped rod-like member, the leading edge of which extends in a direction orthogonal to the second axis $O_2$, while the end of that edge is securely connected to the base end of the second joint unit 3121b. The third joint unit 3121c is connected to the base edge of the approximate L-shape of the second link 3123b.

The third joint unit 3121c has an approximately cylindrical shape, and on the leading end thereof supports the base end of the second link 3123b, so as to allow rotation about a rotation axis (third axis $O_3$) orthogonal to both the first axis $O_1$ and the second axis $O_2$. The leading end of the third link 3123c is securely connected to the base end of the third joint unit 3121c. By rotating the configuration on the leading-end side, including the microscope unit 3110, about the second axis $O_2$ and the third axis $O_3$, the microscope unit 3110 may be moved to change the position of the microscope unit 3110 on the horizontal plane. In other words, controlling the rotation about the second axis $O_2$ and the third axis $O_3$ makes it possible to move the field of view of the captured image on a flat plane.

The third link 3123c is configured to have an approximately cylindrical shape on the leading end side, and on the leading end of the cylindrical shape, the base end of the third joint unit 3121c is securely connected so that both have approximately the same central axis. The base end side of the third link 3123c has a rectangular column shape, and the fourth joint unit 3121d is connected to the end thereof.

The fourth joint unit 3121d has an approximately cylindrical shape, and on the leading end thereof supports the base end of the third link 3123c, so as to allow rotation about a rotation axis (fourth axis $O_4$) orthogonal to the third axis $O_3$. The leading end of the fourth link 3123d is securely connected to the base end of the fourth joint unit 3121d.

The fourth link 3123d is a rod-like member that extends approximately linearly in a direction orthogonal to the fourth axis $O_4$, while also being securely connected to the fourth joint unit 3121d so that the leading end abuts the side face of the approximately cylindrical shape of the fourth joint unit 3121d. The fifth joint unit 3121e is connected to the base end of the fourth link 3123d.

The fifth joint unit 3121e has an approximately cylindrical shape, and on the leading end side thereof supports the base end of the fourth link 3123d, so as to allow rotation about a rotation axis (fifth axis $O_5$) parallel to the fourth axis $O_4$. The leading end of the fifth link 3123e is securely connected to the base end of the fifth joint unit 3121e. The fourth axis $O_4$ and the fifth axis $O_5$ are rotation axes enabling the microscope unit 3110 to be moved in the vertical direction. By rotating the configuration on the leading-end side, including the microscope unit 3110, about the fourth axis $O_4$ and the fifth axis $O_5$, the height of the microscope unit 3110, or in other words the distance between the microscope unit 3110 and the observation target, may be adjusted.

The fifth link 3123e is made up of a combination of a first member having an approximate L-shape with one edge extending in the vertical direction while the other edge extends in the horizontal direction, and a rod-like second member that extends vertically downward from the part of the first member that extends in the horizontal direction. The base end of the fifth joint unit 3121e is securely connected near the top end of the part of the first member that extends in the vertical direction of the fifth link 3123e. The sixth joint unit 3121f is connected to the base end (bottom end) of the second member of the fifth link 3123e.

The sixth joint unit 3121f has an approximately cylindrical shape, and on the leading end side thereof supports the base end of the fifth link 3123e, so as to allow rotation about a rotation axis (sixth axis $O_6$) parallel to the vertical direction. The leading end of the sixth link 3123f is securely connected to the base end of the sixth joint unit 3121f.

The sixth link 3123f is a rod-like member that extends in the vertical direction, with the base end securely connected to the top face of the base unit 3130.

The allowable rotation range of the first joint unit 3121a to the sixth joint unit 3121f is suitably set so that the microscope unit 3110 is capable of making a desired motion. Consequently, in the arm unit 3120 having the configuration described above, three degrees of translational freedom and three degrees of rotational freedom, for a total of six degrees of freedom, may be realized for the motion of the microscope unit 3110. In this way, by configuring the arm unit 3120 so that six degrees of freedom are realized for the motion of the microscope unit 3110, it becomes possible to freely control positions and attitudes of the microscope unit 3110 within the movable range of the arm unit 3120. Consequently, it becomes possible to observe an eye that is an operating site from any angle, and operations may be executed more smoothly.

Note that the configuration of the arm unit 3120 illustrated in the diagram is merely one example, and factors such as the number and the shapes (lengths) of the links constituting the arm unit 3120, as well as the number and arrangement of the joint units and the directions of the rotation axes may be designed suitably so that the desired degrees of freedom may be realized. For example, as described above, to move the microscope unit 3110 freely, the arm unit 3120 preferably is configured to have six degrees of freedom, but the arm unit 3120 may also be configured to have more degrees of freedom (in other words, redundant degrees of freedom). When redundant degrees of freedom exist, in the arm unit 3120, it becomes possible to change the attitude of the arm unit 3120 while keeping the position and the attitude of the microscope unit 3110 in a locked state. Consequently, control that is more convenient to an operator, such as control of the attitude of the arm unit 3120 so that the arm unit 3120 does not interfere with the field of view of the operator looking at the display device 3300, for example, may be realized.

Herein, the first joint unit 3121a to the sixth joint unit 3121f are provided with actuators equipped with a drive mechanism such as a motor, an encoder that detects the rotation angle in each joint unit, and the like. In addition, by having the control device 3200 suitable control driving of each actuator provided for the first joint unit 3121a to the sixth joint unit 3121f, the attitude of the arm unit 3120, or in other words the position and the attitude of the microscope unit 3110, may be controlled. Specifically, the control device 3200 is able to ascertain the current attitude of the arm unit 3120 as well as the current position and attitude of the microscope unit 3110, on the basis of information about the rotation angle of each joint unit detected by the encoder. The control device 3200 uses the ascertained information to compute a control value for each joint unit (such as a rotation angle or a generated torque, for example) so that movement of the microscope unit 3110 corresponding to operation input from the user is realized. Note that at this point, the method by which the control device 3200 controls the arm unit 3120 is not limited, and any of various known control methods, such as force control or position control, may be applied.

For example, by having the operator perform suitable operation input via an input device (not illustrated), the driving of the arm unit 3120 may be suitably controlled by the control device 3200 in accordance with the operation input, and the position and the attitude of the microscope unit 3110 may be controlled. By such control, after moving the microscope unit 3110 from an arbitrary position to an arbitrary position, the microscope unit 3110 may be supported securely at a new position. Note that with regard to the input device, in consideration of the operator's convenience, a device enabling operation even while the operator is holding a surgical instrument in his or her hands, such as a footswitch, for example, is preferably applied. Also, non-contact operation input may also be performed on the basis of gesture detection or line-of-sight detection using wearable device or a camera provided inside the operating room. Consequently, even a user belonging to a clean area is able to operate equipment belonging to an unclean area with a greater degree of freedom. Alternatively, the arm unit 3120 may be operated by what is called a master-slave method. In this case, the arm unit 3120 may be operated remotely by a user via an input device installed at a location separate from the operating room.

Also, if force control is applied, what is called power-assist control may also be conducted, in which external force is received from a user, and the actuators of the first joint unit 3121a to the sixth joint unit 3121f are driven so that the arm unit 3120 moves smoothly in response to the external force. As a result, when the user grasps the microscope unit 3110 to move the position directly, the microscope unit 3110 may be moved with comparatively light force. Consequently, it becomes possible to move the microscope unit 3110 more intuitively with a simpler manipulation, and user convenience may be improved.

In addition, the driving of the arm unit 3120 may be controlled so as to perform a pivot operation when the user manipulates the unit. Herein, a pivot operation refers to an operation of moving the microscope unit 3110 so that the optical axis of the microscope unit 3110 stays pointed at a certain point in a space (hereinafter called the pivot point). A pivot operation makes it possible to observe the same observation position from various directions, thereby making more detailed observation of the lesion possible. Note that if the microscope unit 3110 is configured not to be able to adjust the focus, the pivot operation is preferably performed in a state in which the distance between the microscope unit 3110 and the pivot point is fixed. In this case, it is sufficient to adjust the distance between the microscope unit 3110 and the pivot point to the locked focus distance of the microscope unit 3110. As a result, the microscope unit 3110 moves over the face of a hemisphere centered on the pivot point and having a radius corresponding to the focus distance, and clear captured images are obtained even if the observation direction is changed. On the other hand, if the microscope unit 3110 is configured to be able to adjust the focus, the pivot operation may be performed with a variable distance between the microscope unit 3110 and the pivot point. In this case, for example, the control device 3200 may calculate the distance between the microscope unit 3110 and the pivot point on the basis of information regarding rotation angles of the joint units detected by the encoder and automatically adjust the focus of the microscope unit 3110 on the basis of the calculation result. Alternatively, in a case in which the microscope unit 3110 has the AF function, the focus may be automatically adjusted through the AF function each time the distance between the microscope unit 3110 and the pivot point changes due to a pivot operation.

In addition, the first joint unit 3121a to the sixth joint unit 3121f may also be provided with brakes that restrain rotation. The operation of such brakes may be controlled by the control device 3200. For example, in a case in which it is desirable to lock the position and the attitude of the microscope unit 3110, the control device 3200 applies the brake on each joint unit. As a result, the attitude of the arm unit 3120, or in other words the position and the attitude of the microscope unit 3110, may be locked without driving the actuators, and power consumption may be reduced. In a case in which it is desirable to move the position and the attitude of the microscope unit 3110, it is sufficient for the control device 3200 to release the brake on each joint unit and drive the actuators in accordance with a certain control method.

Such a brake operation may be performed in response to operation input performed by a user via the operating unit 3113 described above. When the user wants to move the position and the attitude of the microscope unit 3110, the user operates the operating unit 3113 to release the brake on each joint unit. As a result, the operating mode of the arm unit 3120 switches to a mode allowing each joint unit to be rotated freely (free mode). Meanwhile, in a case in which the user wants to lock the position and the attitude of the microscope unit 3110, the user operates the operating unit 3113 to apply the brake on each joint unit. As a result, the operating mode of the arm unit 3120 switches to a mode in which the rotation of each joint unit is restrained (locked mode).

The control device 3200 controls operations of the microscope device 3100 and the display device 3300, and thereby controls overall operations of the microscopic operation system 3000. For example, the control device 3200 controls the driving of the arm unit 3120 by causing the actuators of the first joint unit 3121a to the sixth joint unit 3121f to operate in accordance with a certain control method. As another example, the control device 3200 changes the operating mode of the arm unit 3120 by controlling the operation of the brakes of the first joint unit 3121a to the sixth joint unit 3121f. As another example, the control device 3200 performs various types of signal processing on an image signal acquired by the imaging unit of the microscope unit 3110 in the microscope device 3100, and also makes the image data to be displayed on the display device 3300. For the signal processing, any of various known types of signal processing, such as a development process (demosaicing process), an image quality-improving process (such as a band enhancement process, a super-resolution process, a noise reduction (NR) process, and/or a shake correction process), and/or an enlargement process (that is, a digital zoom process), may be performed.

Note that the communication between the control device 3200 and the microscope unit 3110, as well as the communication between the control device 3200 and the first joint unit 3121a to the sixth joint unit 3121f, may be wired communication or wireless communication. In the case of wired communication, communication using electrical signals may be conducted, or optical communication may be conducted. In this case, the transmission cable used for wired communication may be configured as an electrical signal cable, optical fiber, or a composite cable of the two, in accordance with the communication method. Meanwhile, in the case of wireless communication, it is no longer necessary to lay down a transmission cable inside the operating room, and thus a situation in which the movement of medical staff inside the operating room is impeded by such a transmission cable may be resolved.

The control device 3200 may be a processor such as a central processing unit (CPU) or a graphics processing unit (GPU), a control board on which a processor and a storage element such as a memory are both mounted, or the like. As a result of the processor of the control device 3200 operating in accordance with a certain program, the various functions described above may be realized. Note that, in the example illustrated in the diagram, the control device 3200 is provided as a separate device from the microscope device 3100, but the control device 3200 may also be unified with the microscope device 3100, such as by being installed inside the base unit 3130 of the microscope device 3100, for example. Alternatively, the control device 3200 may be made up of multiple devices. For example, by disposing a micro-computer, a control board or the like in the microscope unit 3110 and each of the first joint unit 3121a to the sixth joint unit 3121f of the arm unit 3120, and communicably connecting these control boards to each other, functions similar to the control device 3200 may be realized.

The display device 3300 displays an image corresponding to image data generated by the control device 3200 provided in an operating room under control of the control device 3200. That is, the display device 3300 displays an image of the eye that is an operating site photographed by the microscope unit 3110 thereon. Note that the display device 3300 may also display various kinds of information regarding the operation, for example, physical information of the patient or an operative procedure, instead of or along with the image of the eye. In this case, the display of the display device 3300 may be appropriately switched through a manipulation of the user. Alternatively, a plurality of display devices 3300 may be provided, and the plurality of display devices 3300 may respectively display the image of the eye and the various kinds of information regarding the operation. Any of various known types of display devices, such as a liquid crystal display device or an electroluminescence (EL) display device, for example, may be applied as the display device 3300.

Figure 2:
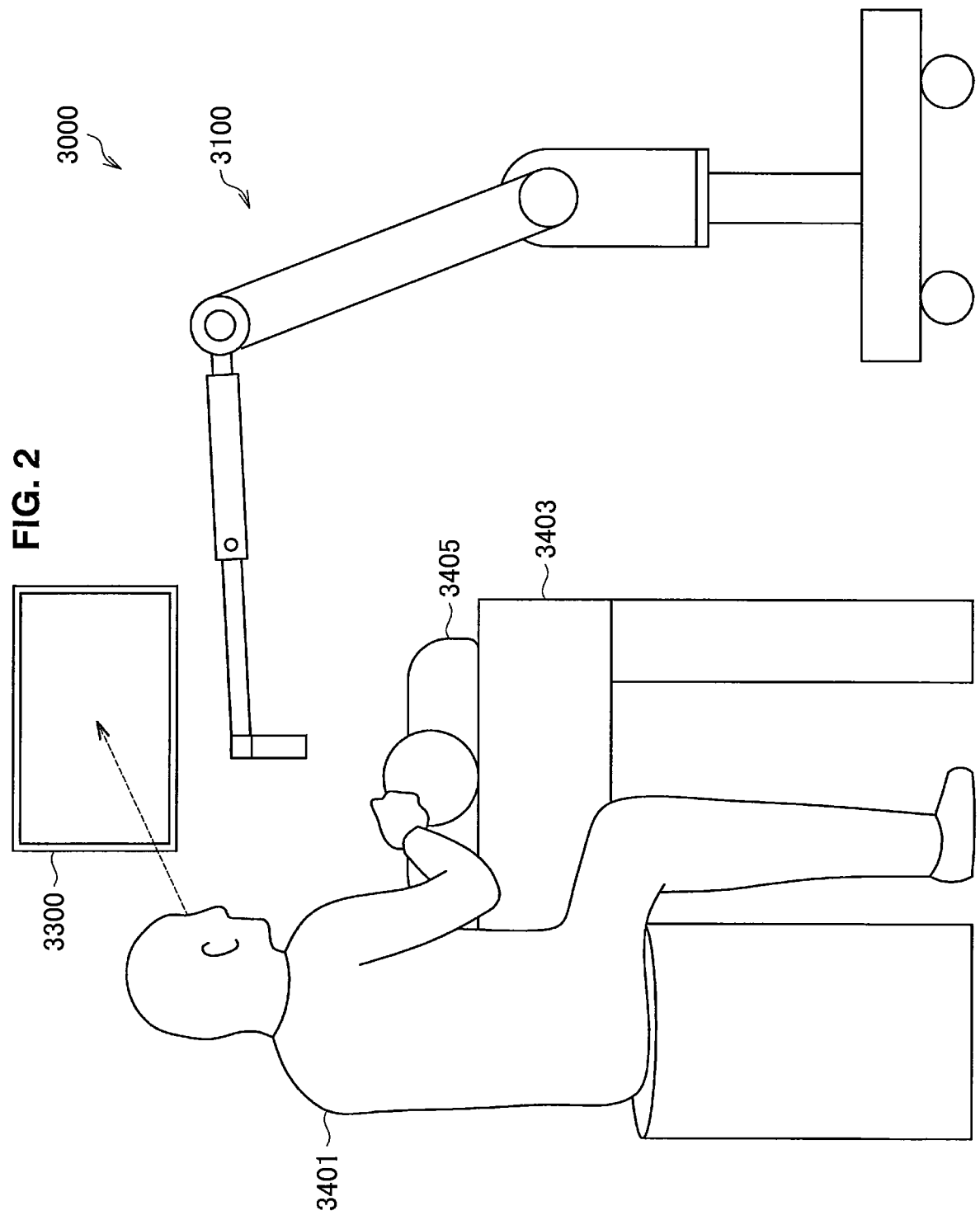
FIG. 2 is a diagram illustrating a state of a operation in which the microscopic operation system illustrated in FIG. 1 is being used.

FIG. 2 is a diagram illustrating a state of an operation in which the microscopic operation system 3000 illustrated in FIG. 1 is being used. FIG. 2 schematically illustrates the state in which an operator 3401 is performing an operation with respect to a patient 3405 lying on a patient bed 3403, using the microscopic operation system 3000. Note that, in FIG. 2, illustration of the control device 3200 is omitted from the configuration of the microscopic operation system 3000 and simplified illustration of the microscope device 3100 is shown for the sake of simplicity.

As illustrated in FIG. 2, an enlarged image of an eye, which is an operating site, photographed by the microscope device 3100 is displayed on the display device 3300 installed on a wall of an operating room using the microscopic operation system 3000 during an operation. The display device 3300 is installed at a position facing the operator 3401, and the operator 3401 performs various kinds of treatment on the eye, observing a state of the eye through the image projected on the display device 3300.

(1-2. Configuration of Drive Control System)

Figure 3:
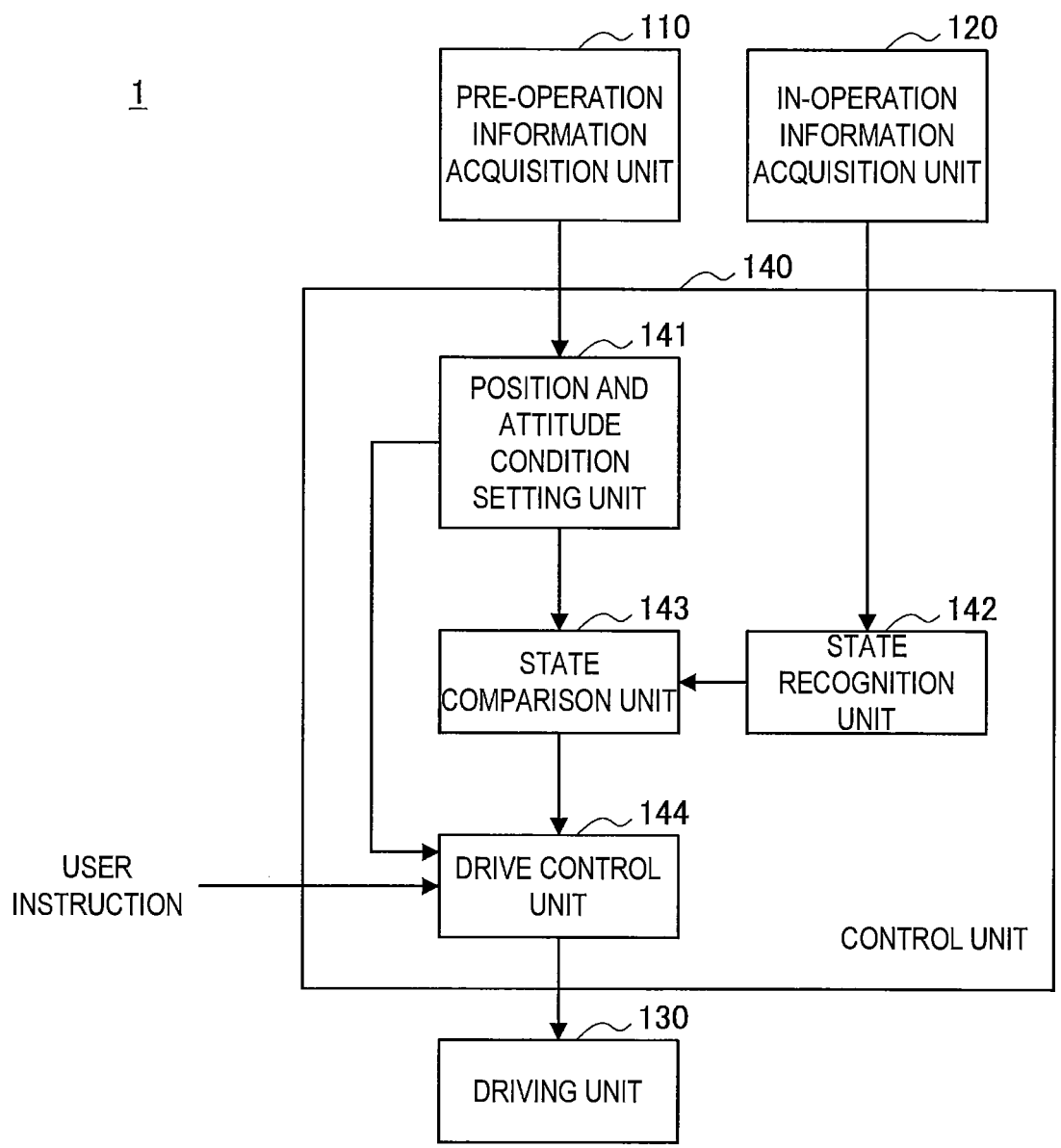
FIG. 3 is a functional block diagram showing an example of a functional configuration of a drive control system according to the first embodiment.

A configuration of a drive control system according to the first embodiment that is applied to the above-described microscopic operation system 3000 will be described with reference to FIG. 3. FIG. 3 is a functional block diagram showing an example of a functional configuration of the drive control system according to the first embodiment.

Here, the drive control system according to the first embodiment is a system that drives the arm unit 3120 of the microscope device 3100 of the microscopic operation system 3000 illustrated in FIG. 1 and controls a position and an attitude of the microscope unit 3110 in order to acquire a captured image of an operating site that a user desires when an operation starts. That is, the drive control system is a system that automatically moves the microscope unit 3110 to an initial position at which the desired captured image of the eye is likely to be obtained when an operation starts. A series of control steps performed in the drive control system according to the first embodiment to automatically move a position and an attitude of the microscope unit 3110 to the initial position will also be referred to as initial operation control below.

The initial operation control of the drive control system is started in accordance with an instruction of a user. That is, an operation mode of the arm unit 3120 is in neither the above-described full mode nor the locked mode, but is a so-called automatic operation mode while the drive control system is activated and performs the initial operation control. Note that the automatic operation mode can appropriately start and stop in accordance with an instruction of a user.

Referring to FIG. 3, the drive control system 1 according to the first embodiment has a pre-operation information acquisition unit 110, an in-operation information acquisition unit 120, a driving unit 130, and a control unit 140 for its functions.

The pre-operation information acquisition unit 110 is constituted by input devices of various kinds (a touch panel, a remote controller, and the like) provided in the microscopic operation system 3000. The pre-operation information acquisition unit 110 acquires information regarding position and attitude conditions that are conditions that prescribe a position and an attitude of the microscope unit 3110 with respect to an operating site to obtain a desired captured image of a user before the operation. Specifically, the position and attitude conditions are set to at least include information with which a position and an attitude of the microscope unit 3110 with respect to the eye, which is an operating site, can be uniquely determined. In the first embodiment, the position and attitude conditions at least include an instruction regarding an appearance of an image of the eye in the captured image (a position of the image of the eye in the captured image, a size of the image of the eye in the captured image, a vertex direction in the captured image, or the like) and/or an instruction regarding a photographing direction of the eye (a positional relationship between an eye axis and an optical axis of the microscope unit 3110). Here, in the first embodiment, a value determined by the drive control system 1 is determined as a magnification factor of an optical zoom and an electronic zoom of the microscope unit 3110. Thus, if the appearance of the image and the photographing direction are designated as position and attitude conditions, a position and an attitude of the microscope unit 3110 with respect to the eye for realizing the conditions can be uniquely determined.

Note that the instructions included in the position and attitude conditions may overlap each other. For example, in the above-described example, the appearance of the image may also include information regarding photographing direction, such as whether the eye is being viewed from vertically above or in a direction slightly oblique from vertically above. Thus, in the first embodiment, levels of priority may be set for the instructions included in the position and attitude conditions. These levels of priority may be appropriately set by a user when the position and attitude conditions, which will be described below, are registered. In a case in which the instructions included in the position and attitude conditions overlap each other, a drive control unit 14 of the control unit 140, which will be described below, controls a position and an attitude of the microscope unit 3110 so that an instruction having a higher level of priority is prioritized. For example, in a case in which a level of priority of the appearance of the image is set to be higher than that of the photographing direction, a position and an attitude of the microscope unit 3110 can be controlled such that a captured image sufficiently approximates an instructed appearance of the image while the photographing direction is set to as close to an instructed direction (e.g., a vertically downward direction) as possible. Alternatively, in a case in which a level of priority of the photographing direction is set to be higher to certainly fulfill an instruction regarding the photographing direction, a position and an attitude of the microscope unit 3110 can be controlled such that the captured image approximates an instructed appearance of the image as closely as possible while realizing the photographing direction.

In the drive control system 1, for example, a plurality of sets of different position and attitude conditions are registered in a storage unit (not illustrated) provided in the drive control system 1 in advance and a user designates his or her desired position and attitude conditions among the sets of conditions, and thereby the pre-operation information acquisition unit 110 can acquire the position and attitude conditions.

FIG. 4 illustrates an example of a graphical user interface (GUI) when position and attitude conditions are designated.

FIG. 4 is a diagram illustrating an example of the GUI when position and attitude conditions are designated. As illustrated in FIG. 4, for example, a plurality of different position and attitude conditions are displayed using icons 203 on a display screen 201 constituting the pre-operation information acquisition unit 110. Each of the icons 203 describes the name of an operator and a location (an upper part or an ear-side part) of the eye to be incised in the illustrated example. When the display screen 201 is integrated with a touch panel and the user touches one of the icons 203, for example, a position and attitude condition corresponding to the icon 203 can be designated. Note that control of displaying the display of the above-described GUI illustrated in FIG. 4 on the display screen 201 constituting the pre-operation information acquisition unit 110 can be executed by the control unit 140.

Figure 5:
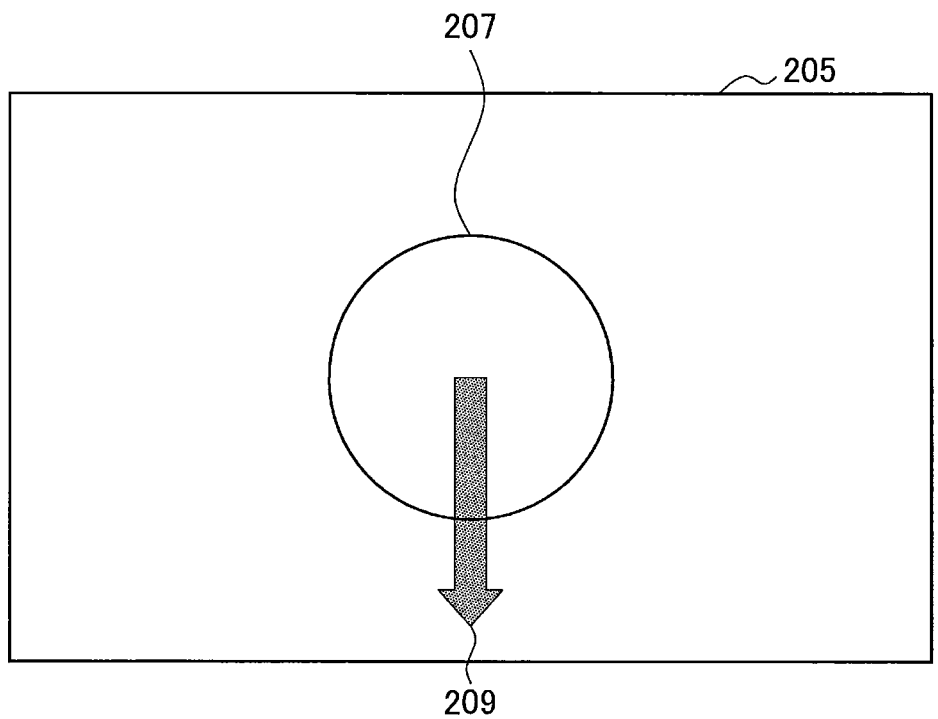
FIG. 5 is a diagram illustrating an example of a GUI on which position and attitude conditions are registered.
Figure 6:
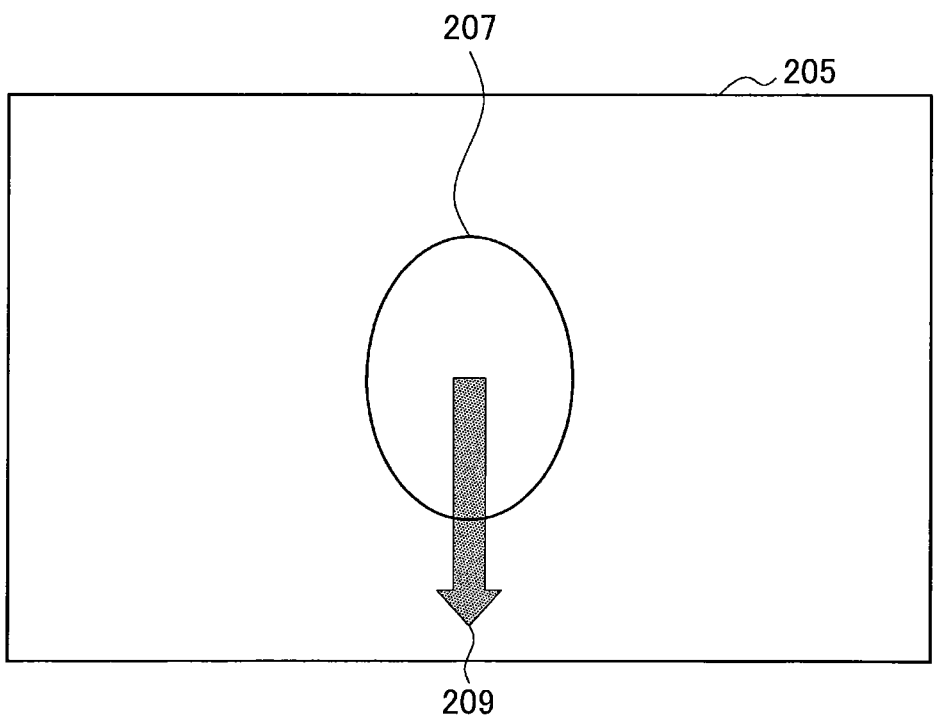
FIG. 6 is a diagram illustrating an example of a GUI on which position and attitude conditions are registered.
Figure 7:
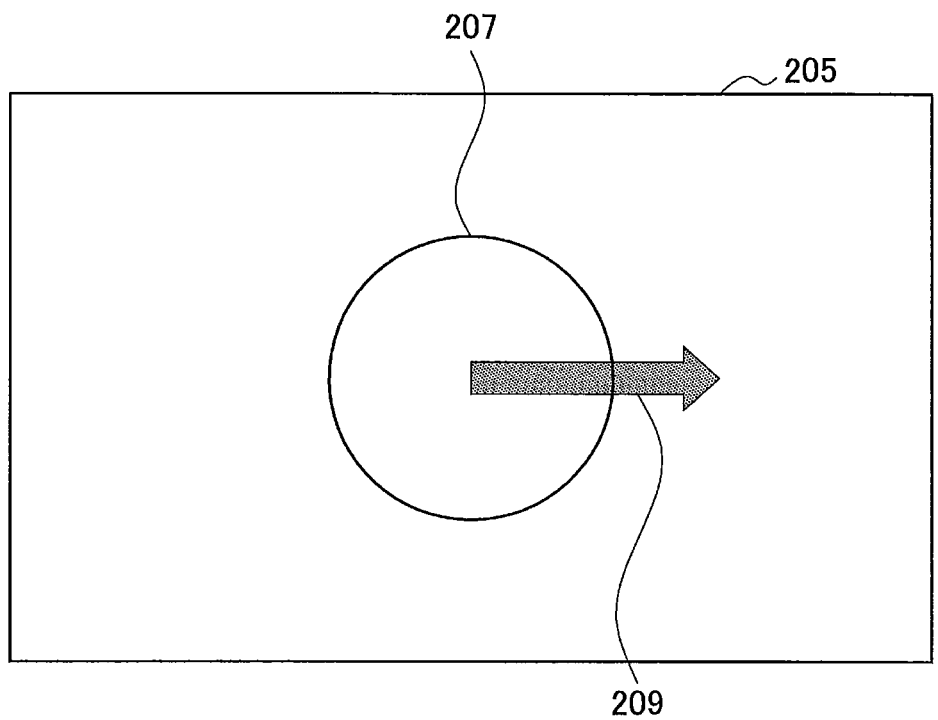
FIG. 7 is a diagram illustrating an example of a GUI on which position and attitude conditions are registered.

In addition, when position and attitude conditions respectively corresponding to the icons 203 are to be registered in the storage unit in advance, for example, the user can perform the registration using a GUI illustrated in FIGS. 5 to 7. FIGS. 5 to 7 are diagrams illustrating an example of the GUI when position and attitude conditions are registered. In FIGS. 5 to 7, the GUI for registering an instruction regarding an appearance of an image included in a position and attitude condition is illustrated as an example.

For example, a circle 207 indicating a corneal ring portion and an arrow 209 indicating a vertex direction of the patient are displayed on a display screen 205 in the GUI as illustrated in FIGS. 5 to 7. A position, a size, and a roundness of the displayed circle 207 can be appropriately modified in accordance with a manipulation of the user. The position of the circle 207 indicates a position of the corneal ring portion in a displayed captured image that has been actually photographed by the microscope unit 3110 during an operation. The size of the circle 207 indicates a size of the corneal ring portion in the displayed captured image that has been actually photographed by the microscope unit 3110 during the operation. In addition, the roundness of the circle 207 indicates a shape and a photographing direction of the corneal ring portion in the displayed captured image that has been actually photographed by the microscope unit 3110 during the operation. If the circle 207 is substantially a perfect circle as illustrated in FIGS. 5 and 7, for example, the roundness thereof indicates that the photographing direction of the microscope unit 3110 is substantially vertically downward. In addition, if the circle 207 is an ellipse as illustrated in FIG. 6, the roundness thereof indicates that the photographing direction of the microscope unit is a direction slightly oblique with respect to the vertically downward direction. The user appropriately adjusts the position, the size, and the roundness of the circle 207 to reproduce a captured image that he or she wants to view during the operation.

In addition, a direction of the displayed arrow 209 can be appropriately modified in accordance with a manipulation of the user. The direction of the arrow 209 indicates a vertex direction of the patient in the displayed captured image that has been actually captured by the microscope unit 3110 during the operation. The user appropriately adjusts the direction of the arrow 209 to reproduce a captured image that he or she wants to view during the operation.

The display examples illustrated in FIGS. 5 to 7 show several examples in which the circle 207 and the arrow 209 are disposed after the user completes adjustment. A position and attitude condition corresponding to the display example illustrated in FIG. 5 can be, for example, a position and attitude condition corresponding to an upward incision. In a case in which position and attitude conditions are registered in accordance with the display example illustrated in FIG. 5 and the initial operation control is performed on the basis of these position and attitude conditions, the microscope unit 3110 photographs the eye to position the vertex part on a lower side of the imaging screen and the photographing direction is substantially vertically downward.

In addition, a position and attitude condition corresponding to the display example illustrated in FIG. 6 can be, for example, a position and attitude condition corresponding to an upward incision, as in the display example illustrated in FIG. 5. However, in a case in which the position and attitude condition is registered in accordance with the display example illustrated in FIG. 6 and the initial operation control is performed on the basis of the position and attitude condition, the eye is photographed to position the vertex part on the lower side of the imaging screen and the photographing direction is a direction slightly oblique with respect to the vertically downward direction.

In addition, a position and attitude condition corresponding to the display example illustrated in FIG. 7 can be, for example, a position and attitude condition corresponding to an incision to an ear side. In a case in which the position and attitude condition is registered in accordance with the display example illustrated in FIG. 7 and the initial operation control is performed on the basis of the position and attitude condition, the eye is photographed to position the vertex part on a right side of the imaging screen and the photographing direction is substantially vertically downward.

The state of the circle 207 and the arrow 209 after the user completes adjustment are registered in the storage unit as an instruction regarding an appearance of an image included in the position and attitude condition. Since the user can intuitively register the appearance of the image that he or she wants to obtain during the operation using the GUI, the position and attitude condition can be registered more simply. Note that the control of displaying the above-described display using the GUI illustrated in FIGS. 5 to 7 on the display screen 205 can be executed by the control unit 140. In addition, the display screen 205 may be a display screen of the display device constituting the pre-operation information acquisition unit 110, or a display screen of a separate display device provided in the drive control system 1.

The pre-operation information acquisition unit 110 provides information regarding the position and attitude condition acquired before the operation to a position and attitude condition setting unit 141 of the control unit 140 which will be described below.

The in-operation information acquisition unit 120 acquires various kinds of information necessary for controlling a position and an attitude of the microscope unit 3110 during the operation (which will also be referred to as in-operation information below). The in-operation information may be information indicating a positional relationship between the eye that is the operating site and the microscope unit 3110. The in-operation information acquisition unit 120 is configured by the microscope unit 3110, and at least acquires information regarding a captured image (captured image information) as the in-operation information. In addition, the microscopic operation system 3000 may also include a marker (e.g., a magnetic marker) provided in the vertex direction of the patient bed 3403 and a sensor (e.g., a magnetic sensor) that detects the marker, and the in-operation information acquisition unit 120 may be configured to include the marker and the sensor. In that case, the in-operation information acquisition unit 120 can acquire information regarding a relative position corresponding to the head part of the patient bed 3403 with respect to the microscope unit 3110 on the basis of a detection value of the sensor as the in-operation information.

The in-operation information acquisition unit 120 acquires the in-operation information when necessary during an operation. Note that, according to the above-described example, acquisition of captured image information and acquisition of information regarding a relative position of the patient bed 3403 may be performed together at all times, or appropriately switched between in a time sequence so that only one kind of information is acquired.

The in-operation information acquisition unit 120 provides the acquired in-operation information to a state recognition unit 142 of the control unit 140 which will be described below.

The driving unit 130 is constituted by an actuator provided in each joint unit of the arm unit 3120 of the microscope device 3100. The driving unit 130 is driven under control of a drive control unit 144 of the control unit 140, which will be described below, so that a position and attitude condition is satisfied on the basis of a captured image acquired during the operation. Accordingly, the arm unit 3120 is driven and a position and an attitude of the microscope unit 3110 can be controlled so that a desired captured image that satisfies the position and attitude condition is obtained.

The control unit 140 is configured by the control device 3200, and comprehensively controls processes performed in the drive control system 1. The control unit 140 has the position and attitude condition setting unit 141, the state recognition unit 142, a state comparison unit 143, and the drive control unit 144 for its functions. These functions can be realized through operations of a processor included in the control unit 140 in accordance with a predetermined program.

The position and attitude condition setting unit 141 sets the position and attitude condition on the basis of information regarding the position and attitude condition acquired before the operation provided from the pre-operation information acquisition unit 110. Specifically, the position and attitude condition setting unit 141 extracts a feature amount of a desired captured image corresponding to the position and attitude condition from the information regarding the position and attitude condition and stores a parameter indicating the feature amount. The parameter is, for example, a center position of the ellipse or the circle corresponding to the corneal ring portion in the captured image, a long diameter and a short diameter of the ellipse or the circle corresponding to the corneal ring portion in the captured image, a long axis direction of the ellipse or the circle corresponding to the corneal ring portion in the captured image, a vertex direction in the captured image, or the like.

The position and attitude condition setting unit 141 provides the information regarding the set position and attitude condition (i.e., information regarding the extracted feature amount (the parameter) to the state comparison unit 143 and the drive control unit 144.

The state recognition unit 142 recognizes a state of a current captured image acquired by the microscope unit 3110 on the basis of the in-operation information provided from the in-operation information acquisition unit 120. The state of the captured image can be information corresponding to the position and attitude condition included in the captured image, i.e., an appearance of an image of the eye included in the captured image, and a photographing direction in the captured image. The state recognition unit 142 recognizes the state on the basis of the captured image information provided from the in-operation information acquisition unit 120 using any of various kinds of image recognition technology. At this time, in a case in which the in-operation information provided from the in-operation information acquisition unit 120 includes information regarding a relative position of the patient bed 3403 based on a detection value of a magnetic sensor or the like, the state recognition unit 142 may recognize a rough position of the eye and the vertex direction in the captured image on the basis of information regarding the position of the patient bed 3403.

The state recognition unit 142 provides information regarding the recognized state of the current captured image to the state comparison unit 143 and the drive control unit 144.

The state comparison unit 143 compares the position and attitude condition set by the user before the operation and the state of the current captured image recognized by the state recognition unit 142, and determines whether the state of the current captured image approximates the state of the desired captured image corresponding to the position and attitude condition. Specifically, the state comparison unit 143 extracts a feature amount of the current captured image on the basis of the information regarding the state of the current captured image provided by the state recognition unit 142, similar to the extracted feature amount of the desired captured image corresponding to the above-described position and attitude condition. Then, whether the state of the current captured image approximates the state of the desired captured image corresponding to the position and attitude condition is determined by comparing the feature amounts of the images with each other.

In a case in which the states of both images are determined to be distant from each other, the state comparison unit 143 issues an instruction to the drive control unit 144 to drive the arm unit 3120 so that the desired captured image corresponding to the position and attitude condition is obtained. On the other hand, in a case in which the states of both images are determined to approximate each other, the determination indicates that an image that sufficiently approximates the desired captured image has already been captured, and thus the state comparison unit 143 ends the process without issuing any particular instruction to the drive control unit 144.

In a case in which an instruction has been received from the state comparison unit 143, the drive control unit 144 drives the driving unit 130 on the basis of the information regarding the position and attitude condition set before the operation provided from the position and attitude condition setting unit 141 and the information regarding the state of the current captured image provided from the state recognition unit 142 so that the position and attitude condition is satisfied, and thereby the position and the attitude of the microscope unit 3110 are updated. The in-operation information acquisition unit 120 acquires in-operation information again with respect to the updated new position and attitude, and a state recognition process and a state comparison process are performed by the state recognition unit 142 and the state comparison unit 143 respectively again on the basis of the in-operation information.

In addition, the drive control unit 144 may drive the driving unit 130 in accordance with an instruction given from outside by a user to change the position and the attitude of the microscope unit 3110. For example, when a series of processes relating to the above-described initial operation control is started, the drive control unit 144 may drive the driving unit 130 in accordance with the instruction from the user to move the position and the attitude of the microscope unit 3110 to an initial position (search start position) and an initial attitude (search start attitude) at which the series of processes relating to the initial operation control is started.

The configuration of the drive control system 1 according to the first embodiment has been described above. Note that the function of the control unit 140 will be described again in more detail with reference to FIG. 8.

(1-3. Processing Sequence of Control Method)

Figure 8:
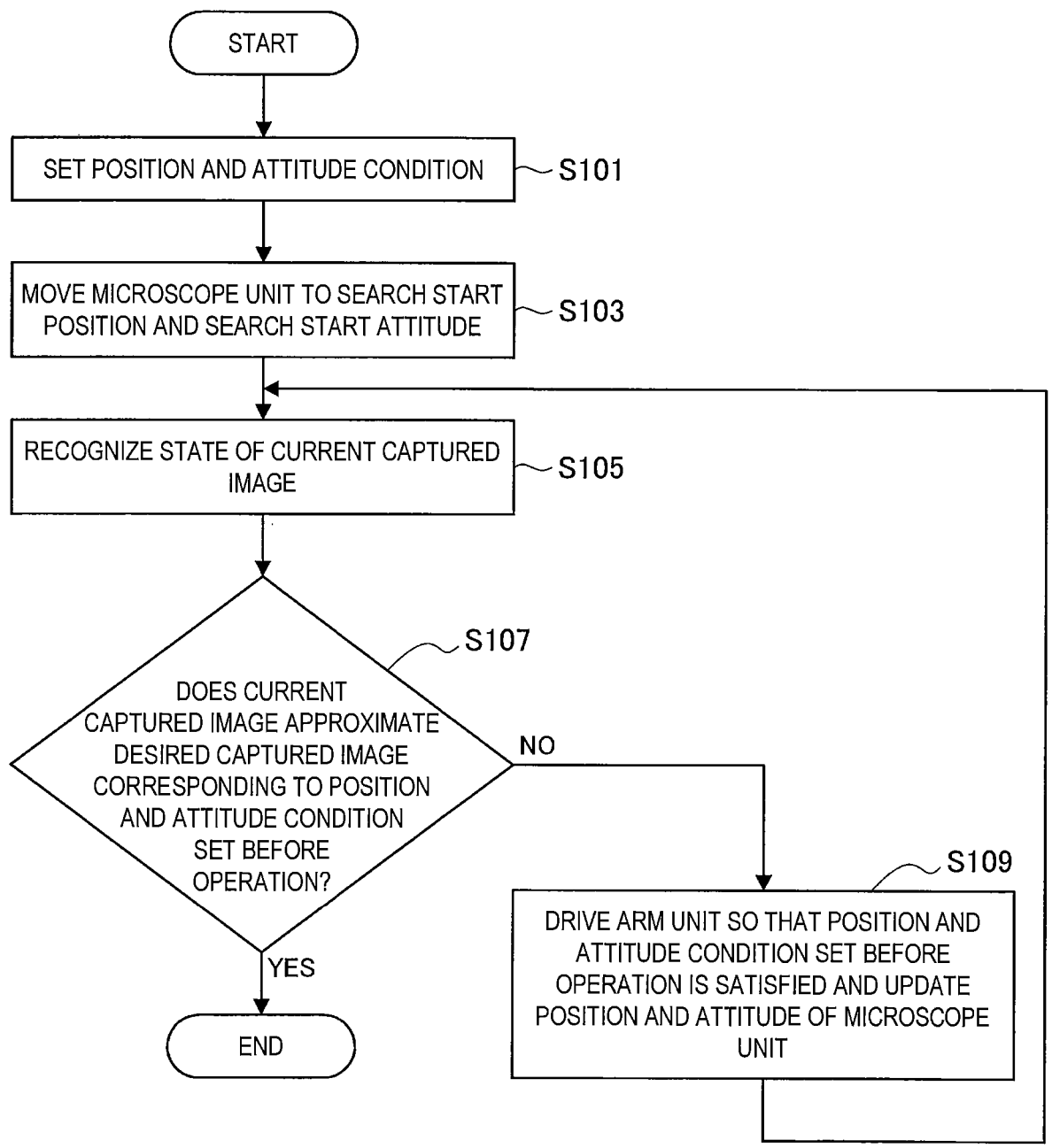
FIG. 8 is a flowchart showing an example of a processing sequence of a control method according to the first embodiment.

A processing sequence of a control method according to the first embodiment will be described with reference to FIG. 8. FIG. 8 is a flowchart showing an example of the processing sequence of the control method according to the first embodiment. Note that the processes shown in FIG. 8 correspond to processes executed by the control unit 140 of the above-described drive control system 1 illustrated in FIG. 3.

Referring to FIG. 8, first, a position and attitude condition is set in accordance with an input of a user before an operation (Step S101) in the control method according to the first embodiment. The process of Step S101 corresponds to the process executed by the position and attitude condition setting unit 141 illustrated in FIG. 3. Note that, since the position and attitude condition has been described above in detail, description thereof is omitted here.

Next, the microscope unit 3110 is moved to take a search start position and a search start attitude in accordance with an instruction of the user on a start of initial operation control (Step S103). The process of Step S103 corresponds to the process executed by the drive control unit 144 illustrated in FIG. 3.

Figure 9:
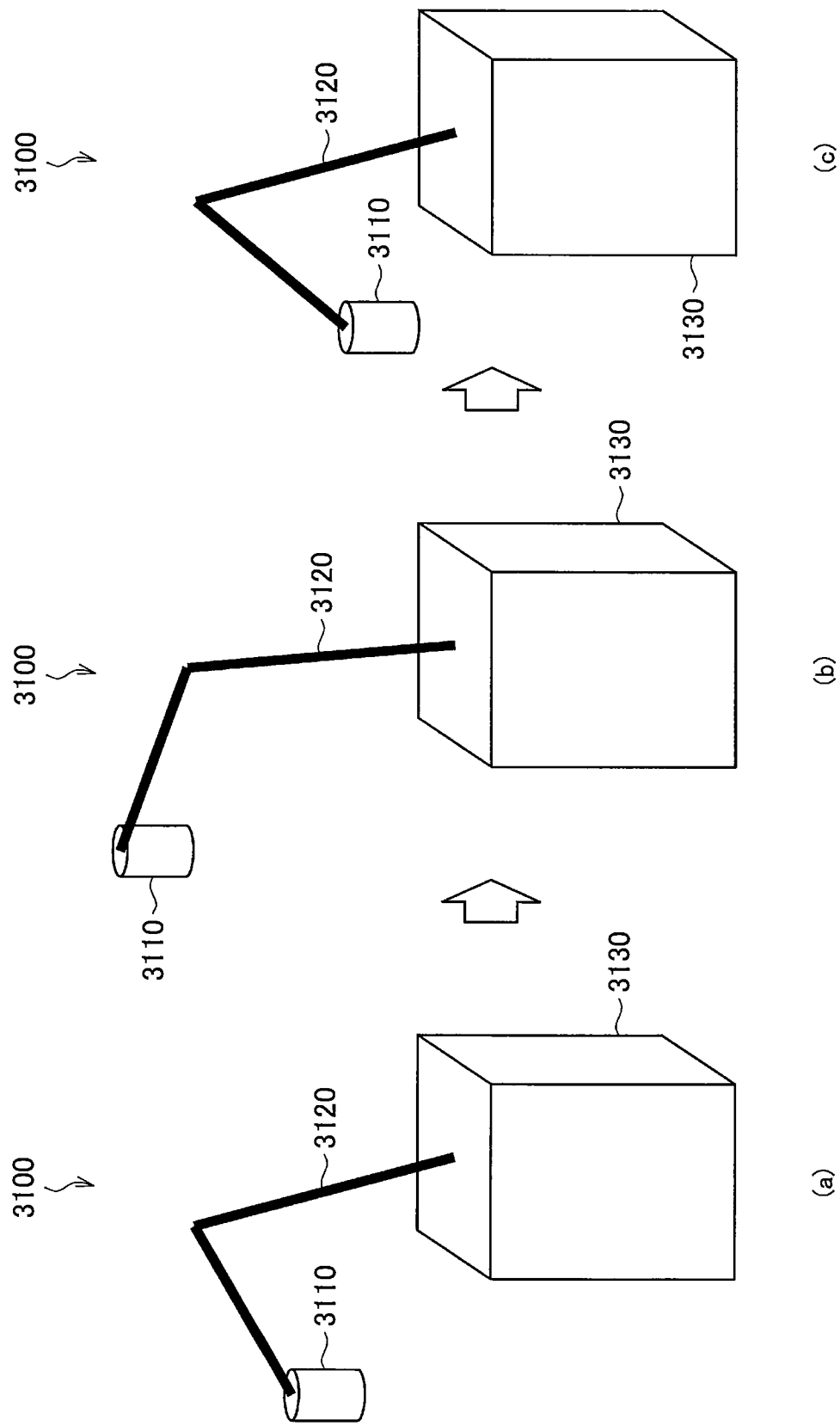
FIG. 9 is a diagram for describing a search start position and a search start attitude.

FIG. 9 is a diagram for describing a search start position and a search start attitude. In FIG. 9, simplified illustration of the microscope device 3100 illustrated in FIG. 1 is shown for the sake of simplicity.

FIG. 9(*a*) shows a position and an attitude of the microscope unit 3110 before the drive control system 1 starts the initial operation control, i.e., at the time of receipt or delivery. In the first embodiment, the position and the attitude of the microscope unit 3110 before the initial operation control is started may not be fixed.

The microscope unit 3110 is moved to the search start position and the search start attitude from the above-described state in accordance with an instruction of the user that the initial operation control be started (FIG. 9(*b*)). The search start position and the search start attitude are a position and an attitude in which the microscope unit is placed immediately above and relatively higher than the patient bed 3403 and the optical axis is oriented in a vertically downward direction, as illustrated in FIG. 9(*b*). Normally in ophthalmic surgery, the patient 3405 lies on his or her side face up on the patient bed 3403 and the operation is performed on the patient having his or her eye oriented in a vertically upward direction in most cases (see FIG. 2), and thus a captured image overlooking a range including the eye can be obtained by setting the search start position, and the search start attitude as described above. Here, a prescribed value of magnification factor of the microscope unit 3110 is stipulated in the first embodiment as described above. However, after the microscope unit 3110 is moved to the search start position and the search start attitude in Step S103, an eye detection process can be performed in a process of ascertaining a state of a current captured image (Step S105) as will be described below. Thus, when the microscope unit 3110 is moved to the search start position and the search start attitude, a magnification factor of the microscope unit 3110 may be automatically set to have as wide an angle as possible, regardless of the stipulated value. Accordingly, a likelihood that an eye will be included in the captured image at the search start position and the search start attitude increases, and thus the eye detection process can be performed more efficiently. Note that, when a process of updating the position and the attitude of the microscope unit 3110 is performed in Step S109 in this case, as will be described below, the magnification factor of the microscope unit 3110 may be adjusted to the stipulated value at an appropriate timing.

Note that the above-described search start position and search start attitude are merely examples, and the search start position and the search start attitude may be appropriately set by the user in accordance with an operative procedure in the first embodiment.

In addition, the drive control unit 144 may control the position and the attitude of the microscope unit 3110 before the start of the initial operation control so that the position and the attitude of the microscope unit 3110 at the time of receipt or delivery become the same as the search start position and the search start attitude. In this case, the process of Step S103 can be appropriately omitted.

Furthermore, the search start position and the search start attitude may not be set in advance, and the user may perform a manual manipulation to move the microscope unit 3110 to an arbitrary position and attitude at which the eye is likely to be included in the captured image, instead of the process of Step S103.

When the microscope unit 3110 is moved to the search start position and the search start attitude in Step S101, a state of a current captured image is recognized on the basis of the in-operation information (Step S105). The process of Step S105 corresponds to the process executed by the state recognition unit 142 illustrated in FIG. 3. Note that, since the in-operation information has been described above in detail, description thereof is omitted here.

Specifically, a position of the eye is first detected from captured image information included in the in-operation information in Step S105. Any of various known image recognition technologies may be used in the process.

Figure 10:
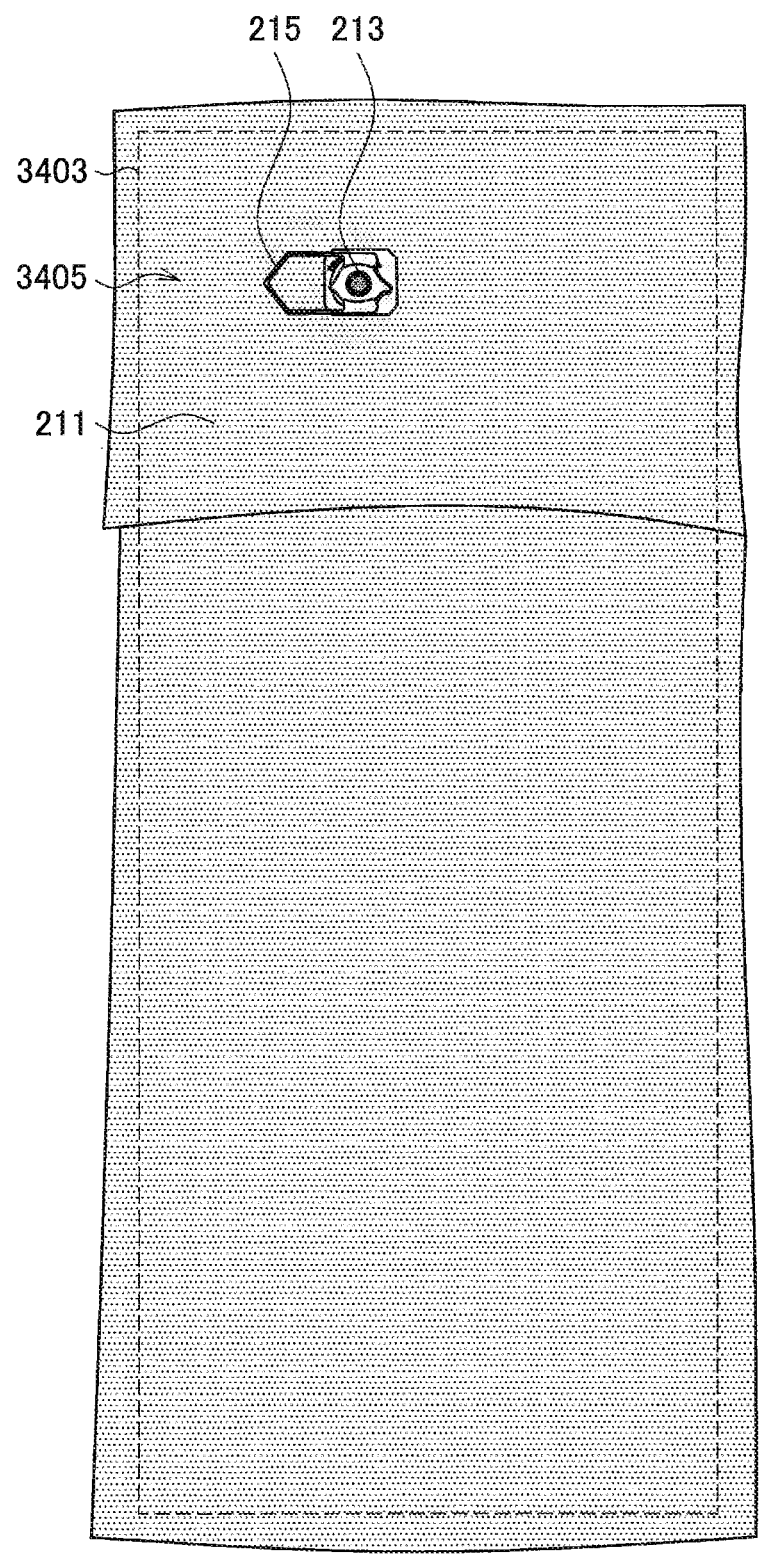
FIG. 10 is a diagram for describing an eye position detection process on the basis of a captured image.
Figure 11:
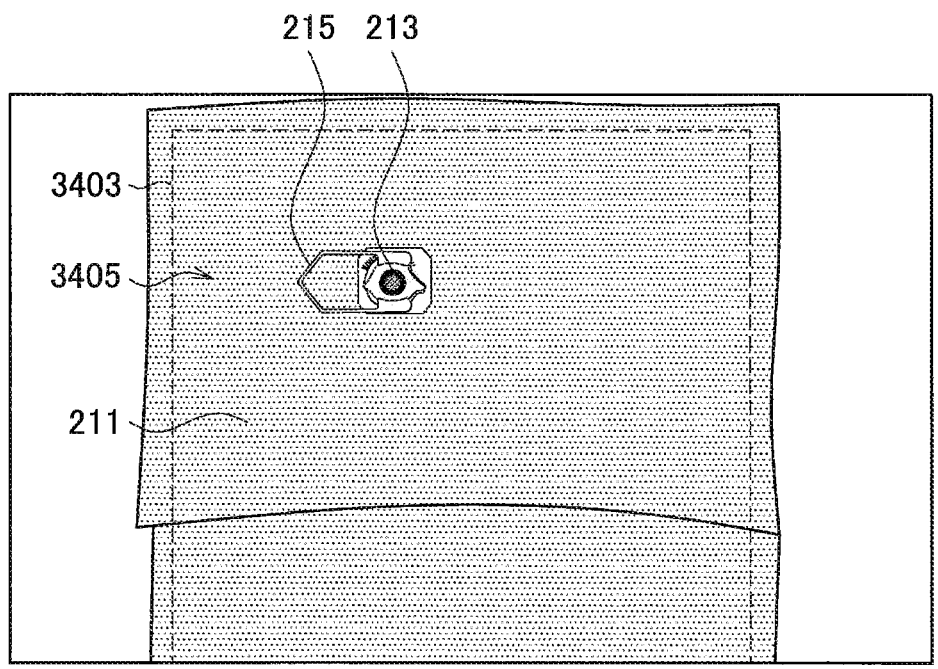
FIG. 11 is a diagram for describing an eye position detection process on the basis of a captured image.
Figure 12:
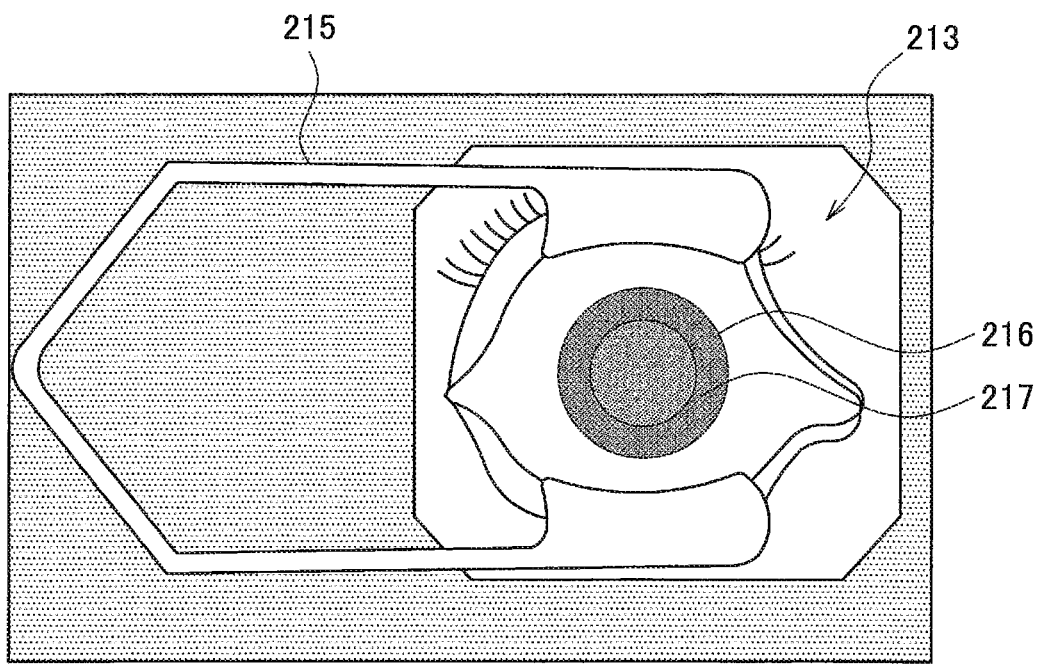
FIG. 12 is a diagram for describing an eye position detection process on the basis of a captured image.

FIGS. 10 to 12 are diagrams for describing a process of detecting a position of the eye on the basis of a captured image. FIG. 10 schematically illustrates a state of the patient 3405 lying on the patient bed 3403 viewed from above during ophthalmic surgery. A drape 211 covers the entire body of the patient 3405 who is lying on his or her back on the patient bed 3403 during the ophthalmic surgery as illustrated in FIG. 10. The drape 211 has an opening at a position corresponding to the eye 213 that is the operating site to expose only the eye 213 therethrough. An instrument 215 keeps the eye 213 open during the operation.

FIG. 11 illustrates an example of a captured image captured by the microscope unit 3110 at a search start position and a search start attitude. As illustrated in FIG. 11, for example, an image overlooking the head of the patient and its vicinity from above is obtained at the search start position and the search start attitude. The eye 213 can be detected in the captured image by detecting, for example, the white of the eye from the color of the drape 211. Note that, in a case in which the in-operation information includes information regarding a relative position of the patient bed 3403 on the basis of a detection value of a magnetic sensor or the like, a rough position of the eye 213 may be detected on the basis of the information.

When the position of the eye 213 is detected in Step S105, then a corneal ring portion and a vertex direction are detected in the image of the eye 213 included in the captured image. FIG. 12 illustrates an example of the image of the eye 213 included in the captured image captured by the microscope unit 3110. As illustrated in FIG. 12, a corneal ring portion 216 is the boundary between the white of the eye and the iris 217, and thus the corneal ring portion 216 can be detected by detecting a change in color in the image of the eye 213 and specifying the boundary on which the color changes.

In addition, the vertex direction can be detected by recording patterns of blood vessels and the iris 217 of the eye 213 of the patient 3405 included in a captured image of the eye 213 captured at a sitting position in advance and comparing the pre-recorded patterns with patterns thereof that are recognized in an image of the eye 213 included in another captured image captured by the microscope unit 3110. Alternatively, in a case in which a captured image that is likely to include a positional relationship between the drape 211 and the eye 213 as illustrated in FIG. 11 is obtained, a direction of the body of the patient 3405 may be identified from the positional relationship and then the vertex direction may be detected on the basis of the direction of the body. Further alternatively, in a case in which the in-operation information includes information regarding a relative position of the head of the patient bed 3403 based on a detection value of a magnetic sensor or the like, the vertex direction may be detected on the basis of this information.

When the state of the current captured image is recognized in Step S105, it is then determined whether the current captured image approximates a desired captured image corresponding to a position and attitude condition set before the operation (Step S107). The process of Step S107 corresponds to the process executed by the state comparison unit 143 illustrated in FIG. 3.

Specifically, in Step S107, a feature amount of the current captured image is extracted from the state of the captured image recognized in Step S105. The feature amount is extracted as a parameter similar to a parameter indicating a feature amount of the desired captured image corresponding to the above-described position and attitude condition (e.g., a center position of an ellipse or a circle corresponding to the corneal ring portion of the captured image, lengths of a long diameter and a short diameter of the ellipse or the circle corresponding to the corneal ring portion of the captured image, a long axis direction of the ellipse or the circle corresponding to the corneal ring portion of the captured image, the vertex direction in the captured image, etc.). Then, using an appropriate evaluation function with the parameters as variables, degrees of matching with respect to instructed details included in the position and attitude condition (specifically, a degree of matching of an appearance of an image under the position and attitude condition set before the operation with an appearance of the current captured image, and a degree of matching of a photographing direction under the position and attitude condition set before the operation with a photographing direction in the current captured image) are calculated as distance indicators.

In a case in which all of the distance indicators are smaller than a predetermined threshold value, the state of the current captured image is determined to sufficiently approximate the state of the desired captured image corresponding to the position and attitude condition. Since this case indicates that an image that sufficiently approximates the desired captured image has already been captured, the series of process ends. An example of the position and the attitude of the microscope unit 3110 at the time point at which the series of processes ends (i.e., the time point at which the initial operation control ends) is illustrated in FIG. 9(c).

On the other hand, in a case in which any one of the calculated range indices is greater than the predetermined threshold value, the state of the current captured image is determined to be distant from the state of the desired captured image corresponding to the position and attitude condition. In that case, the process proceeds to Step S109.

Note that levels of priority can be included in an instruction included in the position and attitude condition as described above. In the case in which levels of priority are included in an instruction included in the position and attitude condition, the threshold value with respect to the above-described range indices may be changed in accordance with the levels of priority for each instruction. For example, in a case in which a level of priority of an appearance of an image is set to be higher than that of a photographing direction, a threshold value with respect to a distance indicator indicating a degree of coincidence of the appearance of the image may be lower than a threshold value with respect to a distance indicator indicting a degree of coincidence of the photographing direction.

In Step S109, the arm unit 3120 is driven so that the position and attitude condition set before the operation is satisfied, and thus the position and the attitude of the microscope unit 3110 are updated. Then, returning to Step S105, the processes of Step S105 and Step S107 are repeated in the updated new position and attitude. Note that the process of Step S109 corresponds to the process executed by the drive control unit 144 illustrated in FIG. 3.

Specifically in Step S109, specific details of the updating (i.e., an amount of movement of the microscope unit 3110) can be set on the basis of the position and attitude of the microscope unit 3110 at the time point and a state of a captured image acquired at the time point. For example, in a case in which the microscope unit 3110 is in a position and an attitude that approximate the search start position and the search start attitude, the position of the microscope unit 3110 is moved to position the eye 213 at the center of the captured image due to the movement in the horizontal direction with the height and the attitude of the microscope unit 3110 maintained. In addition, in a case in which the eye 213 reaches the center of the captured image and the magnification factor of the microscope unit 3110 is changed to have a wide angle at the search start position and the search start attitude, for example, the magnification factor is changed such that that of the microscope unit 3110 has the value stipulated for the drive control system 1. Further, in a case in which the above-described task is achieved, for example, the microscope unit 3110 approaches the eye 213 until the size of the eye 213 in the captured image approximates a size of the eye (a size of the corneal ring portion) in the appearance of the image included in the position and attitude condition set before the operation. Further, in a case in which the above-described task is achieved, for example, the position and the attitude of the microscope unit 3110 are finely adjusted so as to approximate the appearance of the image and the photographing direction included in the position and attitude condition set before the operation.

However, a time is taken to move the microscope unit 3110 to the final position and attitude in the above-described phased movement. Thus, actually, the final position and attitude, a movement route to the final position and attitude, a movement time taken to reach the final position and attitude, and the like are predicted and the position and attitude of the microscope unit 3110 may be updated to reduce the movement time to the shortest time on the basis of the prediction result.

The processing sequence of the control method according to the first embodiment has been described above.

Here, a position and an attitude of a microscope unit are in general adjusted by a user using his or her hand in a operation in which a microscope device is used so far. For example, the user grabs the microscope unit by himself or herself and moves the microscope unit to an approximate position, then finely adjusts the position of the microscope unit using a foot pedal powered by electricity, and thereby adjusts a position and an attitude of the microscope. Complicated work that takes a fair time is necessary to adjust the position and the attitude of the microscope unit, which imposes a burden on the user as described above. In particular, in a case in which photographing is performed with a high magnification factor, a significant change is shown in a captured image only by slightly changing a position and an attitude of the microscope unit, and thus adjustment for obtaining a desired captured image needs to be more delicate, and thus a work time and a burden of the user further increases. An increase in the work time means a lengthened operation time, which also increases a burden of a patient.

With regard to the above-described matter, the microscope unit 3110 can be automatically moved to a position and an attitude at which the desired captured image is obtained when the operation starts, as described above according to the first embodiment. Thus, the user can obtain the desired captured image more easily without spending time and efforts in adjustment. Therefore, a shortened operation time and a reduced burden of the user and the patient can be realized.

2. Second Embodiment

A second embodiment of the present disclosure will be described. In the initial operation control according to the above-described first embodiment, in the case in which the state of the current captured image obtained by the microscope unit 3110 is determined to approximate the state of the desired captured image corresponding to the position and attitude condition set before the operation, the series of processes performed in the drive control system 1 ends. That is, in the initial operation control according to the first embodiment, driving control of the microscope unit 3110 by the drive control system 1 ends at the time point at which the position and the attitude of the microscope unit 3110 are controlled so that the set position and attitude condition are satisfied. Meanwhile, the eye may move due to autokinesis of the patient 3405 or treatment of the operator 3401 during the operation. In such a case, it is desirable to continuously control the position and attitude of the microscope unit 3110 so that the position and attitude condition is further satisfied even when the eye has been moved and the movement of the eye is traced, depending on an operative procedure or details of the position and attitude condition.

Thus, in the second embodiment, a drive control system is configured such that a position and an attitude of the microscope unit 3110 at which a position and attitude condition is likely to be satisfied are continuously controlled until a user issues an end instruction, rather than ending the control at a time point at which the position and attitude condition is satisfied once. Accordingly, in the second embodiment, desired captured images corresponding to the position and attitude condition are continuously obtained even when the eye is moved, and thus user convenience can be improved. Note that control of the drive control system according to the second embodiment in which a position and an attitude of the microscope unit 3110 are automatically moved so that the position and attitude condition is satisfied while movement of the eye is traced until an end instruction is input will also be referred to as trace operation control.

Note that the drive control system according to the second embodiment executes processes similar to those in the first embodiment except that a trigger for ending control is different. Thus, differences of the second embodiment from the first embodiment will be mainly described below, and detailed description of overlapping matters with the first embodiment will be omitted.

(2-1. Configuration of Drive Control System)

Figure 13:
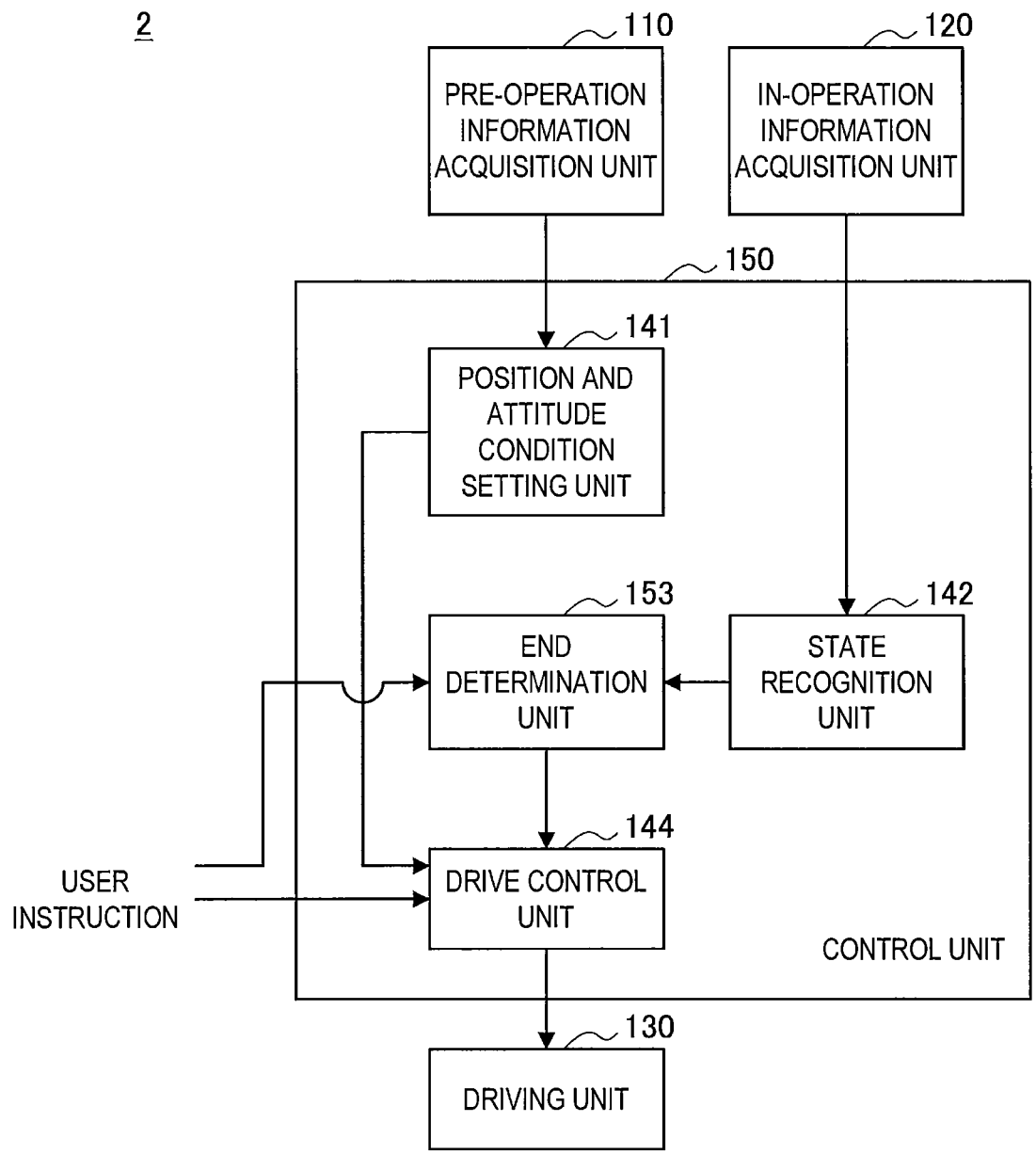
FIG. 13 is a functional block diagram showing an example of a functional configuration of a drive control system according to a second embodiment.

A configuration of the drive control system according to the second embodiment applied to the above-described microscopic operation system 3000 will be described with reference to FIG. 13. FIG. 13 is a functional block diagram showing an example of a functional configuration of the drive control system according to the second embodiment.

Referring to FIG. 13, the drive control system 2 according to the second embodiment has the pre-operation information acquisition unit 110, the in-operation information acquisition unit 120, the driving unit 130, and a control unit 150 for its functions. Note that, since functions of the pre-operation information acquisition unit 110, the in-operation information acquisition unit 120, and the driving unit 130 are similar to those of the first embodiment, detailed description thereof will be omitted here.

The control unit 150 has the position and attitude condition setting unit 141, the state recognition unit 142, an end determination unit 153, and the drive control unit 144 for its functions. These functions can be realized by a processor constituting the control unit 150 that operates in accordance with a predetermined program. Note that, since the functions of the position and attitude condition setting unit 141, the state recognition unit 142, and the drive control unit 144 are similar to those of the first embodiment, detailed description will be omitted here.

The end determination unit 153 determines whether there is an instruction issued from a user to end the trace operation control. In a case in which there is no end instruction, the end determination unit 153 issues an instruction to drive the arm unit 3120 to the drive control unit 144 so that a desired captured image corresponding to a position and attitude condition is obtained. The drive control unit 144 drives the driving unit 130 complying with the instruction so that the position and attitude condition set before an operation is satisfied, and thereby a position and an attitude of the microscope unit 3110 are updated. The in-operation information acquisition unit 120 acquires in-operation information at the updated new position and attitude and the state recognition unit 142 performs a state recognition process again on the basis of the in-operation information. On the other hand, in a case in which it is determined that there is an end instruction, the process ends without a particular instruction issued by the end determination unit 153 to the drive control unit 144.

The configuration of the drive control system 2 according to the second embodiment has been described above.

(2-2. Processing Sequence of Control Method)

Figure 14:
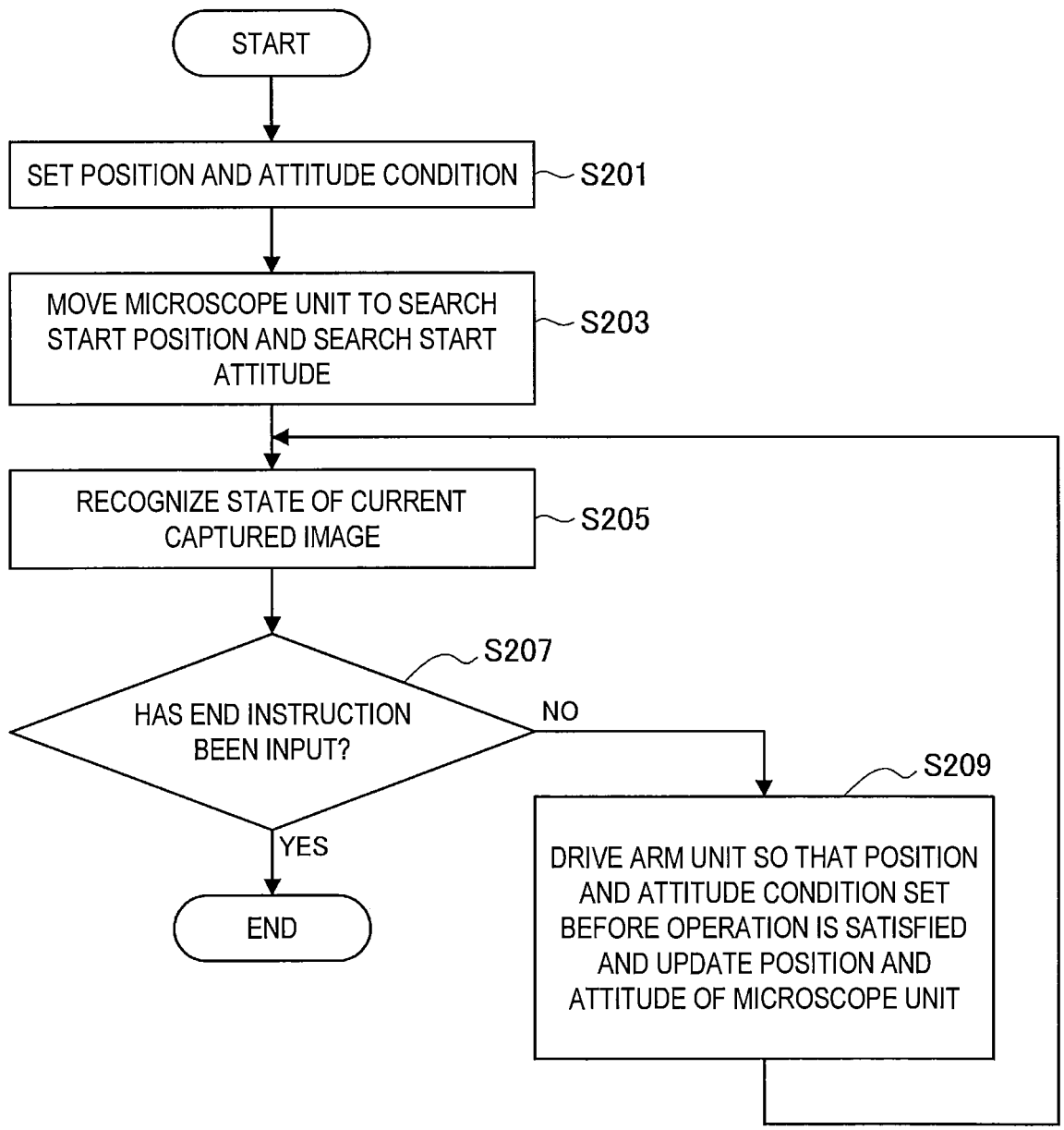
FIG. 14 is a flowchart showing an example of a processing sequence of a control method according to the second embodiment.

A processing sequence of a control method according to the second embodiment will be described with reference to FIG. 14. FIG. 14 is a flowchart showing an example of the processing sequence of the control method according to the second embodiment. Note that the processes shown in FIG. 14 correspond to processes executed by the control unit 150 of the drive control system 2 according to the second embodiment shown in FIG. 13.

Referring to FIG. 14, similar processes to those of Step S101 to Step S105 of the control method according to the first embodiment are executed in Step S201 to Step S205 of the control method according to the second embodiment. That is, a position and attitude condition is set before an operation (Step S201), the microscope unit 3110 is moved to have a search start position and a search start attitude (Step S203), and a state of a current captured image is recognized on the basis of in-operation information (Step S205).

In the control method according to the second embodiment, it is then determined whether the user has input an end instruction, unlike in the first embodiment (Step S207). In a case in which an end instruction is determined to have been input in Step S207, a series of processes end. On the other hand, in a case in which no end instruction is determined to have been input in Step S207, the process proceeds to Step S209. Note that the process of Step S207 corresponds to the process executed by the end determination unit 153 illustrated in FIG. 13.

In Step S209, a similar process to that of Step S109 of the control method according to the first embodiment is executed. That is, the arm unit 3120 is driven so that the position and attitude condition set before the operation is satisfied, and thus the position and the attitude of the microscope unit 3110 are updated. Then, returning to Step S205, the processes of Step S205 and Step S207 are repeated in the updated new position and attitude.

The processing sequence of the control method according to the second embodiment has been described. Also in the second embodiment, the microscope unit 3110 can be automatically moved to a position and an attitude obtained in desired captured image, as in the first embodiment. Thus, similar effect to that of the first embodiment, i.e., a shortened operation time and a reduced burden of the user and the patient can be realized. Further, according to the second embodiment, even in a case in which an eye moves during an operation, the microscope unit 3110 is automatically moved so that the position and attitude condition is satisfied while tracing the movement of the eye. Thus, a desired captured image can be obtained at all times regardless of movement of the eye, and thus user convenience can be improved.

Note that, although the process of moving the microscope unit 3110 to have the search start position and the search start attitude is executed in Step S203 in the example shown in FIG. 14, the second embodiment is not limited thereto. For example, a situation in which the trace operation control according to the second embodiment is executed consecutively after the initial operation control according to the first embodiment ends is also assumed. In this case, a position and an attitude of the microscope unit 3110 might have been controlled such that a desired captured image is substantially obtained at the position and the attitude at the time point at which the trace operation control is about to be executed. If the process of Step S203 is executed in that state, the position and the attitude of the microscope unit 3110 are reset, which is inefficient. Thus, the process of Step S203 may be omitted in the case in which the microscope unit 3110 is expected to have already obtained an image that is close to the desired captured image, as in the case in which the trace operation control is executed consecutively after the initial operation control.

In addition, although the position and the attitude of the microscope unit 3110 can be controlled in accordance with movement of the eye when necessary in the second embodiment, there is concern that, if the microscope unit 3110 is moved even in response to, for example, trivial movement of the eye or regular movement of the eye with very short intervals, unstable captured images are displayed, which rather deteriorates convenience of an operator. The position and the attitude of the microscope unit 3110 may be controlled so as not to trace movement of the eye when the movement of the eye is considered to be trivial. In addition, in a case in which the eye regularly moves with short intervals, an average pattern of movement of the eye within a given time may be taken and the position and the attitude of the microscope unit 3110 may be controlled so as to trace the average pattern. That is, the position and the attitude of the microscope unit 3110 may be controlled so as to trace only extensive movement of the eye.

3. Modified Examples

Several modified examples of the above-described first and second embodiments will be described.

(3-1. Updating of Position and Attitude Condition Through Learning)

In the description above, position and attitude conditions are registered in advance in the drive control systems 1 and 2 and one is appropriately selected therefrom when the initial operation control and the trace operation control are performed. However, in that scheme in which the position and attitude conditions are registered in advance, it can be assumed that a difference exists between a captured image corresponding to a position and attitude condition that has already been registered and an image that a user actually wants to view as a result that an operation is actually performed with the initial operation control or the trace operation control. In this case, after the microscope unit 3110 is moved so that the registered position and attitude condition registered using the initial operation control and the trace operation control is satisfied, an operator has to manually modify the position and the attitude of the microscope unit 3110 to obtain his or her really desired captured image.

In the first and second embodiments, in the case in which an operator manually modifies a position and an attitude of the microscope unit 3110 as described above, a registered position and attitude condition may be updated on the basis of the modification result. That is, the control units 140 and 150 of the drive control systems 1 and 2 may have a function of updating a registered position and attitude condition through learning.

Figure 15:
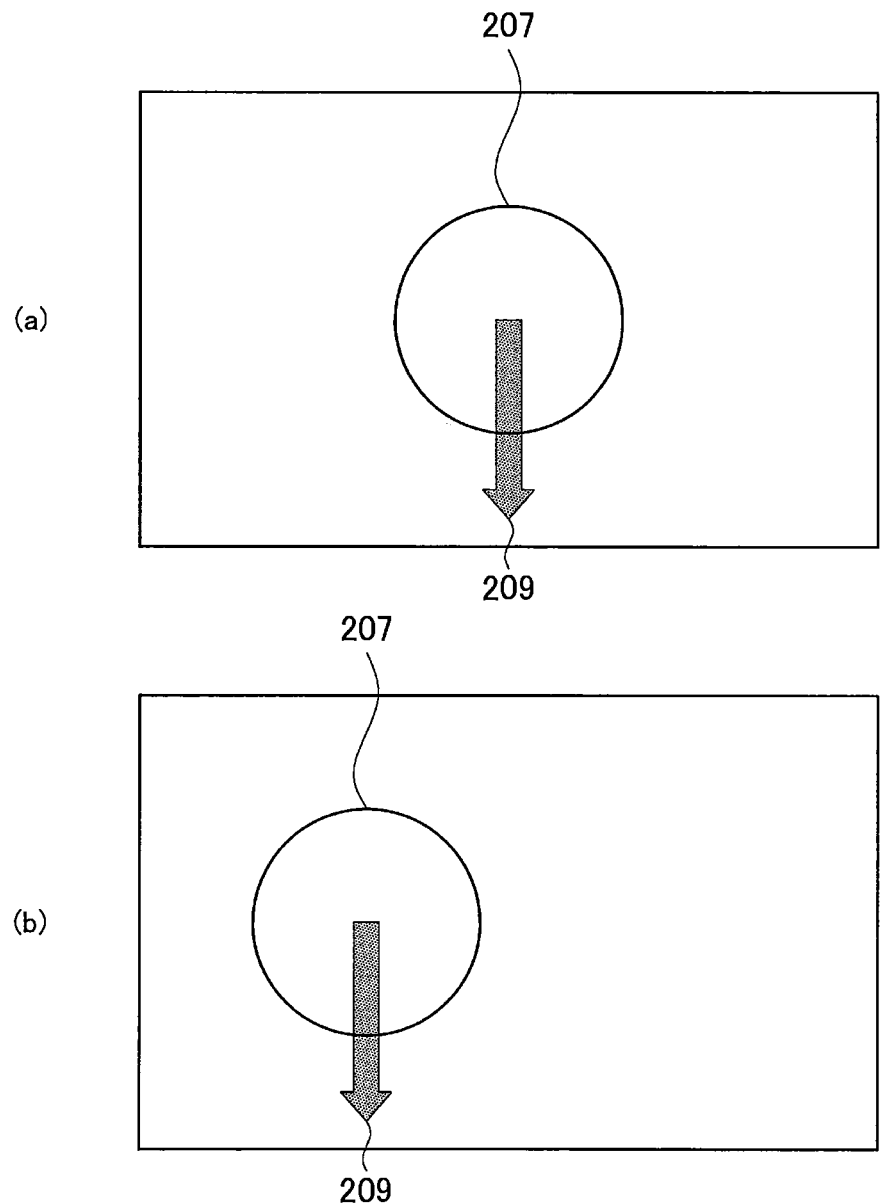
FIG. 15 is a diagram for describing a modification of a position and attitude condition through learning.

Here, a case in which an appearance of an image included in a position and attitude condition is updated through learning will be described as an example. FIG. 15 is a diagram for describing updating of a position and attitude condition through learning. In FIG. 15, the appearance of the image included in the position and attitude condition is illustrated in a similar form to the GUI for registering the appearance of the image described with reference to FIGS. 5 to 7 for the sake of convenience. That is, a circle 207 indicates a corneal ring portion and an arrow 209 indicates a vertex direction in FIG. 15.

FIG. 15 (*a*) illustrates an example of the appearance of the image included in the registered position and attitude condition before learning is performed. Before learning is performed, for example, it is assumed that the appearance of the image, in which the corneal ring portion is positioned substantially at the center of a captured image as illustrated in FIG. 15 (*a*), is registered as a position and attitude condition.

On the other hand, it is assumed that the initial operation control or the trace operation control is performed so that the position and attitude condition including the appearance of the image illustrated in FIG. 15 (*a*) is satisfied and then the operator modifies the position and the attitude of the microscope unit 3110. The appearance of the image corresponding to the modified captured image is illustrated in FIG. 15 (*b*). According to the illustrated example, the corneal ring portion is present at a position slightly deviating to the left from the center of the captured image. Note that the appearance of the image corresponding to the modified captured image can be specified by performing any of various kinds of image recognition processing on the captured image.

In the case in which the operator performs a modification after the initial operation control or the trace operation control as described above, the appearance of the modified image is considered as an appropriate appearance of the image for the operator. Thus, the control units 140 and 150 of the drive control systems 1 and 2 updates instruction details regarding the appearance of the image included in the position and attitude condition set this time with details of the appearance of the modified image. Accordingly, in a case in which the operator designates the position and attitude information and performs the initial operation control or the trace operation control next time, the position and the attitude of the microscope unit 3110 are controlled so as to realize the appearance of the modified image, and thus convenience of the operator can be improved.

Note that learning may be performed practically on the basis of results of a plurality of modifications, rather than a result of one modification. In this case, the control units 140 and 150 may obtain an appearance of a modified average image from appearances of a plurality of images corresponding to modified captured images, which are obtained as a result of the plurality of modifications, and perform updating with a position and attitude condition registered on the basis of the appearance of the average image.

(3-2. Other Example of Instruction Included in Position and Attitude Condition)

An appearance of an image and a photographing direction are exemplified as instructions included in a position and attitude condition in the above description. However, the first and second embodiments are not limited thereto. A position and attitude condition may only include one of the instructions regarding an appearance of an image and a photographing direction. In addition, the position and attitude condition may also include another instruction. For example, the position and attitude condition may include instructions regarding a magnification factor, a distance between the microscope unit and a floor, a distance between the microscope unit and the eye, and/or a direction of the microscope unit 3110 around an optical axis, instead of or in addition to the above-described appearance of the image and/or photographing direction.

Furthermore, the instruction included in the position and attitude condition is registered as a target during control in the above description. In the case of an instruction regarding a photographing direction, for example, a target of the photographing direction, such as a "vertically downward" direction, is registered. However, the first and second embodiments are not limited thereto, and the instruction included in the position and attitude condition may be registered as a restriction during control. A restriction on a photographing direction, for example, "the optical axis of the microscope unit 3110 should be in the range of 10 degrees in a vertically downward direction" may be registered as an instruction regarding a photographing direction.

In addition, the instruction included in the position and attitude condition may be, for example, an instruction that a specific index be maximized or minimized (i.e., a condition that prescribes a position and an attitude of the microscope unit 3110 with respect to an operating site to obtain a desired captured image at which the specific index has a maximum or minimum value). For example, the instruction included in the position and attitude condition may be maximization of transillumination. In this case, in the drive control systems 1 and 2, luminance of reflected light on a retina may be calculated using a captured image photographed by the microscope unit 3110, and maximized transillumination may be determined to be realized when the luminance has a maximum value. Thus, the drive control unit 144 illustrated in FIGS. 3 and 13 specifically updates a position and an attitude of the microscope unit 3110 so that the case of the maximized luminance is searched for while changing a current position and attitude of the microscope unit 3110 in a narrow range, and thus can realize initial operation control and trace operation control in which maximized transillumination is realized. Note that a degree of transillumination and a positional relationship between an eye axis and the optical axis of the microscope unit 3110 are considered to have a predetermined correlation. Thus, when the position and attitude of the microscope unit 3110 at which the above-described luminance has a maximum value are searched for, the microscope unit 3110 may be moved within the range of a predetermined angle (e.g., 15 degrees or narrower) in which an angle formed by the eye axis and the optical axis of the microscope unit 3110 falls.

Alternatively, since a degree of transillumination and a positional relationship between the eye axis and the optical axis of the microscope unit 3110 are considered to have a predetermined correlation as described above, the positional relationship between the eye axis and the optical axis of the microscope unit 3110 in which transillumination has a maximum value may be obtained in advance, and the drive control unit 144 may update the position and attitude of the microscope unit 3110 so that the positional relationship between the eye axis and the optical axis of the microscope unit 3110 in which transillumination has a maximum value is realized at the time of initial operation control and trace operation control. Here, it is known that a positional relationship between an eye axis and an optical axis of a camera when the camera captures the eye can be normally obtained using a positional relationship between a corneal ring portion and a position of a reflection image of light radiated from a point light source, which is disposed at a known position of the camera, on a cornea in a captured image in which the eye is photographed while the point light source radiates light on the eye. Thus, the above-described control can be performed by obtaining the positional relationship between the eye axis and the optical axis of the microscope unit 3110 from the image by the microscope unit 3110 using the above-described method.

Note that, in the case in which the instruction included in the position and attitude condition indicates maximization of transillumination, an instruction regarding a size of the eye may as well be included in the position and attitude condition. As the instruction regarding a size of the eye is included, the microscope unit 3110 can be moved to make substantially no change in the size of the eye in a captured image when the position and attitude of the microscope unit 3110 are updated to maximize transillumination, and thus a further stable image can be provided to a user, without a significant change in display of the captured image.

In addition, at this time, it is desirable to express the instruction regarding the size of the eye with a one-dimensional index such as a length of the eye in the lateral direction or a long axis of a circle corresponding to the corneal ring portion, rather than a two-dimensional index (e.g., a size of a circle corresponding to the corneal ring portion). When the position and attitude of the microscope unit 3110 are updated to maximize transilluminance, it is assumed to move the microscope unit 3110 to change the positional relationship between the eye axis and the optical axis of the microscope unit 3110, i.e., to change the photographing direction; however, if the instruction regarding the size of the eye is expressed with a two-dimensional index, the instruction essentially includes an instruction regarding the photographing direction as well, and thus there is a possibility of the instruction regarding the size of the eye limiting movement of the microscope unit 3110 which is likely to change the photographing direction. With regard to this matter, if the instruction regarding the size of the eye is expressed with a one-dimensional index, the microscope unit 3110 can be moved to change the photographing direction while the size of the eye in the captured image is substantially uniformly maintained, and therefore the position and attitude of the microscope unit 3110 at which transillumination has a maximum value can be more smoothly searched for.

Note that, in a case in which an instruction included in a position and attitude condition is to maximize or minimize a specific index, like the above-described maximization of transillumination, the trace operation control may be preferably performed. When the trace operation control is performed and the eye moves, the microscope unit 3110 is automatically moved to maximize or minimize the specific index designated by the user tracing the movement of the eye, and thus the user can obtain a desired captured image for which the specific index is maximize or minimized at all times.

(3-3. Other Example of Registration Method of Instruction Regarding Appearance of Image)

The instruction regarding the appearance of the image is registered using the GUI illustrated in FIGS. 5 to 7 in the above description. However, the first and second embodiments are not limited thereto, and other GUIs may be used in registration of the instruction regarding appearance of the image. Note that control over display with respect to each of the GUIs which will be described below can be executed by the control units 140 and 150 of the drive control systems 1 and 2 illustrated in FIGS. 3 and 13. In addition, a display screen on which the GUIs are displayed may be the display screen of the display device constituting the pre-operation information acquisition unit 110, or a display screen of a separate display device provided in the drive control systems 1 and 2.

Figure 16:
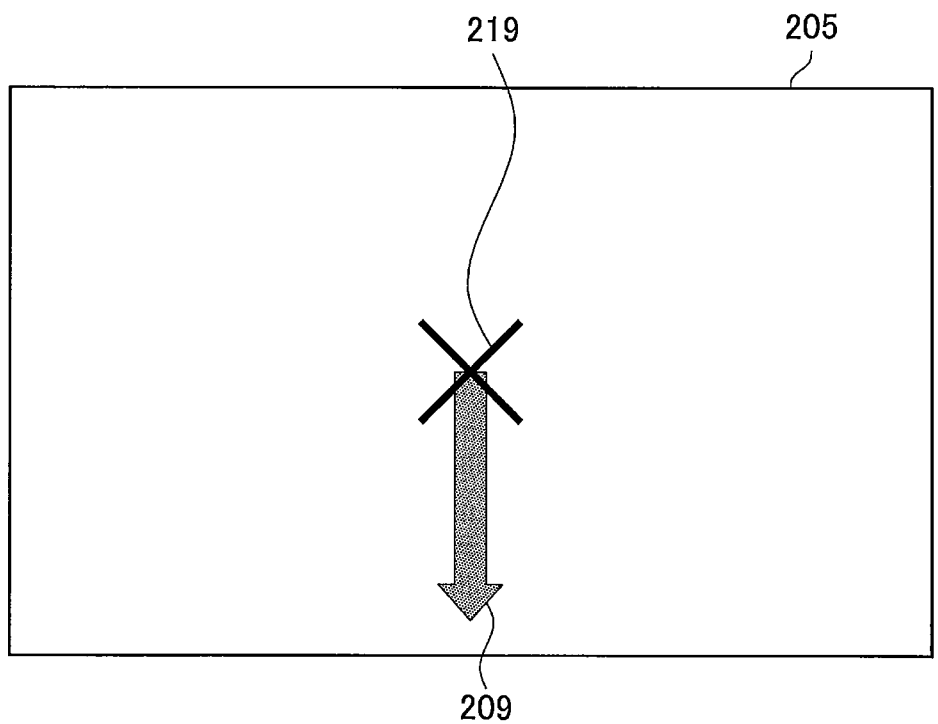
FIG. 16 is a diagram illustrating an example of another GUI for registering an instruction regarding an appearance of an image.
Figure 17:
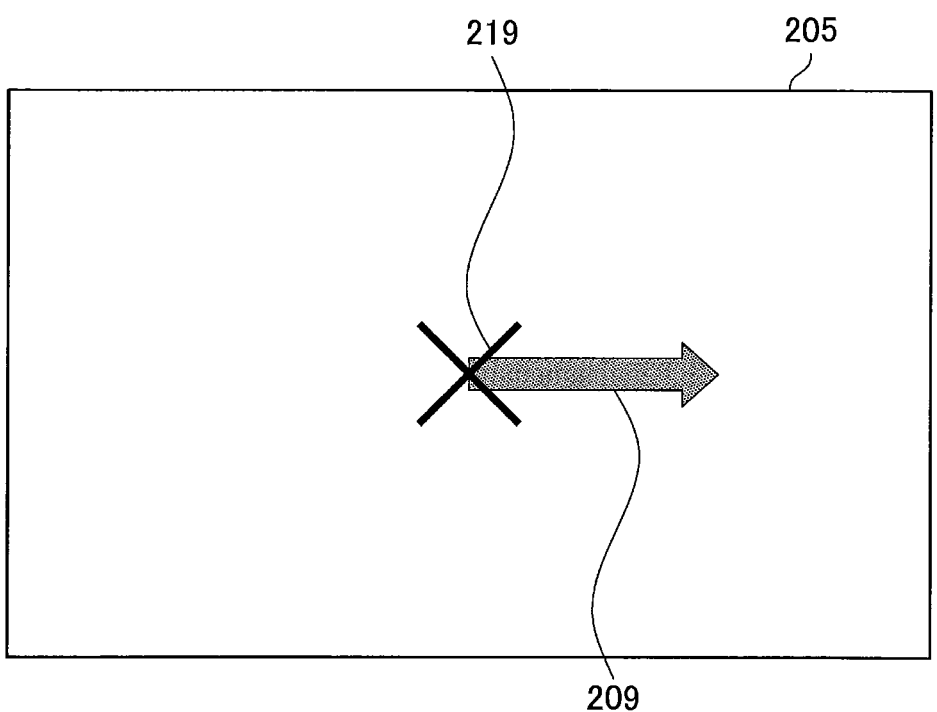
FIG. 17 is a diagram illustrating an example of another GUI for registering an instruction regarding an appearance of an image.

FIGS. 16 and 17 are diagrams illustrating an example of another GUI for registering an instruction regarding an appearance of an image. As illustrated in FIGS. 16 and 17, a mark 219 indicating the center of a cornea and an arrow 209 indicating a vertex direction are displayed on a display screen 205 for the GUI. The arrow 209 is a similar one to the arrow 209 of the GUI illustrated in FIGS. 5 to 7. A user can designate a center position of a corneal ring portion in a captured image and the vertex direction in the captured image by adjusting a position of the mark 219 and a direction of the arrow 209. Designation details can be registered as instructions regarding an appearance of an image. In the illustrated example, the display example of FIG. 16 corresponds to an appearance of an image with respect to upward incision. The display example illustrated in FIG. 17 corresponds to an appearance of an image with respect to an incision to an ear side. When the user designates the center of the cornea and the vertex direction as described above, the instruction regarding the appearance of the image may be registered. Note that, since a size of the eye image is not stipulated in the instruction details using the GUI, instruction details in which the size of the eye image can be stipulated can be separately registered as a position and attitude condition by the user. As instructions in which the size of the eye image can be stipulated, for example, a magnification factor of a captured image, and a distance between the microscope unit 3110 and the eye are exemplified.

Figure 18:
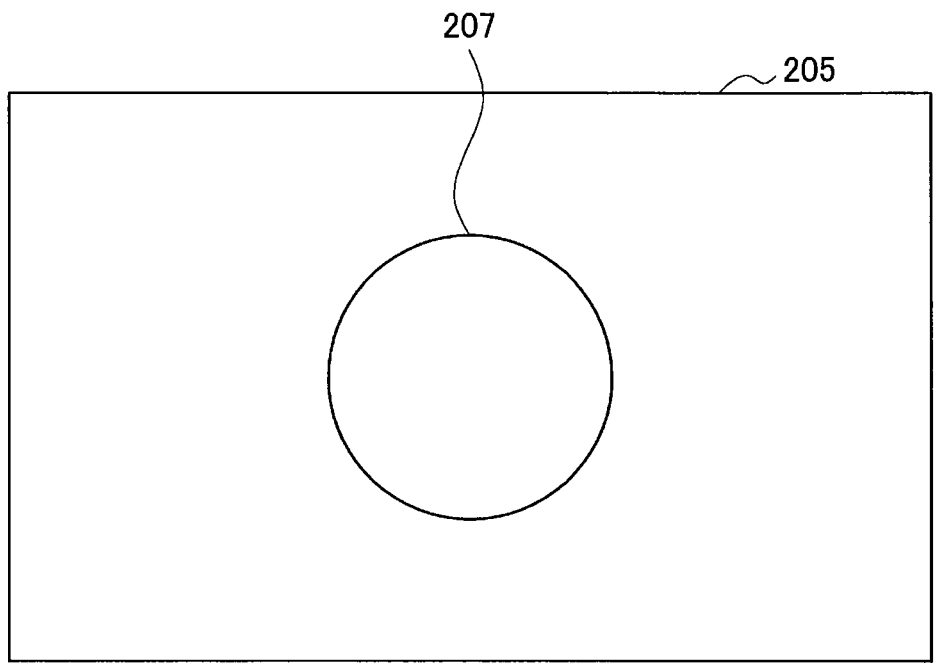
FIG. 18 is a diagram illustrating an example of still another GUI for registering an instruction of an appearance of an image.
Figure 19:
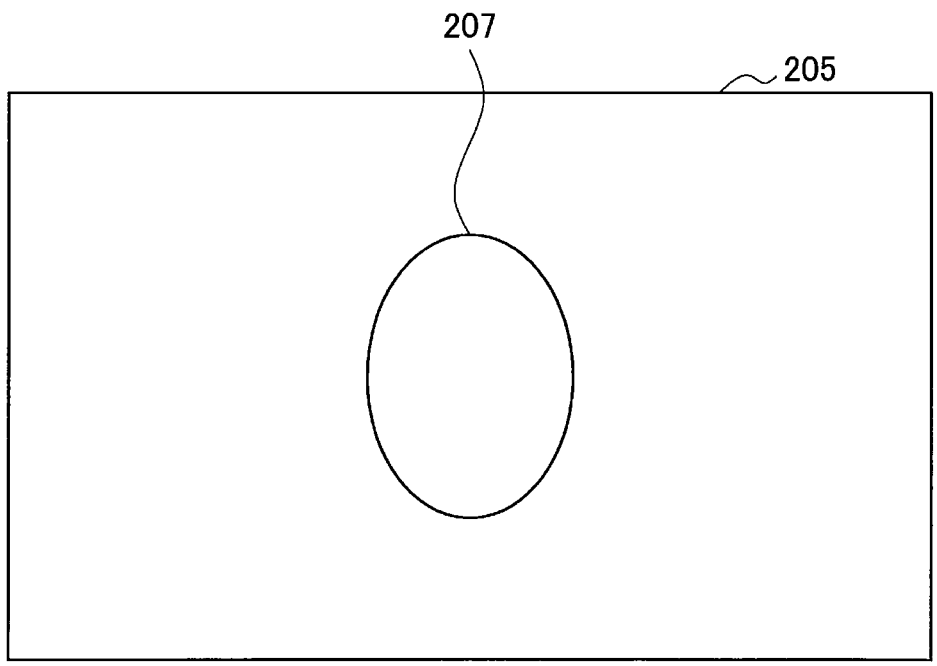
FIG. 19 is a diagram illustrating an example of still another GUI for registering an instruction of an appearance of an image.

FIGS. 18 and 19 are diagrams illustrating an example of still another GUI for registering the instruction regarding the appearance of the image. As illustrated in FIGS. 18 and 19, a circle 207 indicating a corneal ring portion is displayed on the display screen 205 for the GUI. The circle 207 is a similar one to the circle 207 of the GUI illustrated in FIGS. 5 to 7. The user can designate a position of the corneal ring portion in a captured image, a size of the corneal ring portion in the captured image, and a shape (a photographing direction) of the corneal ring portion in the captured image by adjusting a position, a size and a roundness of the circle 207. The designated items can be registered as instructions regarding appearances of the image. The instructions regarding the appearances of the image may be registered by designating the position, the size, and the shape of the corneal ring portion as described above. Note that, since the vertex direction is not stipulated in the instruction details of the GUI in this case, instruction details in which the vertex direction can be stipulated can be separately registered as a position and attitude condition by the user. As an instruction in which the vertex direction can be stipulated, for example, a direction of the microscope unit 3110 around the optical axis is exemplified.

Figure 20:
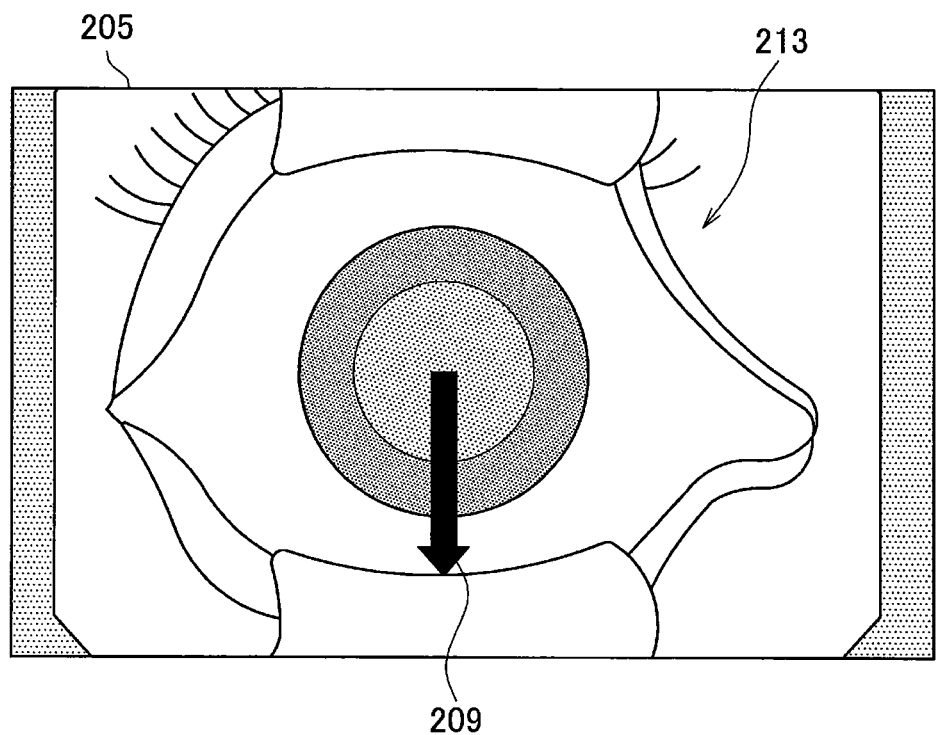
FIG. 20 is a diagram illustrating an example of still another GUI for registering an instruction of an appearance of an image.

FIG. 20 is a diagram illustrating an example of still another GUI for registering the instruction regarding the appearance of the image. As illustrated in FIG. 20, an actual captured image of the eye 213 of the patient 3405 photographed during a past operation is displayed on the display screen 205 for the GUI. In addition, an arrow 209 indicating a vertex direction is displayed being superimposed on the captured image. The arrow 209 is a similar one to the arrow 209 in the GUI illustrated in FIGS. 5 to 7. A size and a position of an image of the eye 213 of the captured image can be appropriately modified in accordance with a manipulation of the user, and the user can designate a position of the eye in a captured image that he or she wants to obtain during an upcoming operation, a size of the eye in the captured image by adjusting the position and the size of the eye 213. In addition, the user can designate the vertex direction in the captured image that he or she wants to obtain during the upcoming operation by adjusting a direction of the arrow 209. These designated items can be registered as instructions regarding appearances of the image. The instructions regarding the appearances of the image may be registered using the GUI for displaying the actual captured image as described above. Using the actual captured image, the user can designate the appearance of the image that he or she wants to obtain during the actual operation to meet his or her assumption and register the designated item as a position and attitude condition. Thus, a desired image can be more surely provided to the user after initial operation control or trace operation control, and thus user convenience can be improved. Note that, an image generated using computer graphics that approximates to the actual eye-capturing image may instead be used, and convenience of this case can be similarly improved to the case in which the actual eye-capturing image is used.

(3-4. Other Example of Designation Method for Position and Attitude Condition)

The position and attitude conditions are designated using the GUI illustrated in FIG. 4 in the above description. The first and second embodiments, however, are not limited thereto and the position and attitude condition may be designated using another method.

For example, before a operation starts, a user may acquire a captured image by controlling a position and an attitude of the microscope unit 3110 using his or her hand in a state in which the patient 3405 is lying down on his or her left or right side on the patient bed 3403 and designate the acquired captured image as an image that the user wants to obtain during the operation. That is, in the present modified example, the pre-operation information acquisition unit 110 illustrated in FIGS. 3 and 13 may include the microscope unit 3110 and an appearance (a position of a corneal ring portion, a size of the corneal ring portion, a vertex direction, and the like) and a photographing direction in a captured image, and the like may be designated as position and attitude conditions on the basis of the image captured by the microscope unit 3110. According to the present modified example, since the position and attitude conditions are designated for the captured image when an operator actually moves the microscope unit 3110, position and attitude conditions can be designated so that a captured image that meets the intension of the user is obtained.

However, in the case in which the position and attitude conditions are designated by manually controlling the position and the attitude of the microscope unit 3110 so that the operator obtains a desired captured image as in the present modified example, it is not necessary to perform initial operation control. Thus, a method for designating the position and attitude conditions according to the present modified example can be appropriately applied when trace operation control is executed.

Note that, in a case in which the method for designating the position and attitude conditions according to the present modified example is applied, the designated position and attitude conditions (i.e., position and attitude conditions based on a captured image acquired through a manipulation of the operator) may be registered in the drive control systems 1 and 2 as prescribed position and attitude conditions that can be used in the future. That is, registration of the position and attitude conditions may be performed using a similar method to the method for designating the position and attitude conditions according to the present modified example. In addition, a registered position and attitude condition may be updated with a position and attitude condition based on a captured image acquired through a manipulation of the operator by combining the method for designating the position and attitude conditions according to the present modified example with the learning process described in (3-1. Updating of position and attitude condition through learning).

(3-5. Restriction on Movement of Microscope Unit)

Control that the microscope unit 3110 is automatically moved so that the position and attitude condition is satisfied is performed in the initial operation control according to the first embodiment and the trace operation control according to the 20 second embodiment. Various kinds of restrictions may be set on the movement of the microscope unit 3110 in the initial operation control and the trace operation control from the perspective of safety in the first and second embodiments.

As such restrictions, for example, setting a lower limit value for a distance between the microscope unit 3110 and an eye, setting a limit on a movable range of the arm unit 3120, setting an upper limit value for movement speed of the microscope unit 3110, and/or limiting joint units to be driven among the joint units of the arm unit 3120 (e.g., driving only several joint units at the leading end side to prevent an attitude of the arm unit 3120 from significantly changing, or the like), and the like are considered.

4. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the case in which the drive control systems 1 and 2 are applied to the ophthalmic surgery and the operating site is eye has been described in the first and second embodiments above, the present technology is not limited thereto. For example, the drive control systems 1 and 2 may be used in various operations to which the microscopic operation system 3000 can be applied, such as a laparotomy. In addition, operating sites to be photographed by the microscope unit 3110 may be diverse in accordance with operations to which the drive control systems 1 and 2 are applied. In a case in which the drive control systems 1 and 2 are applied to another operation, the term "eye" in the above description of the first and second embodiments may be switched to biological tissue corresponding to an operating site of the operation, and processes that constitute the above-described drive control system 1, 2 and performed in the drive control systems 1 and 2 may be executed.

Note that, in a case in which the microscopic operation system 3000 is applied to another operation such as a laparotomy, it is assumed that the biological tissue that is an operating site is larger than the eye, and a position of the microscope unit 3110 is somewhat significantly changed during the operation to facilitate observation of the biological tissue in different positions and directions. However, in the initial operation control and the trace operation control according to the above-described first and second embodiments, the microscope unit 3110 is automatically moved so that the one designated position and attitude condition is satisfied. Thus, if the initial operation control and the trace operation control are applied to the other operation, it is necessary to designate a new position and attitude condition each time the position of the microscope unit 3110 is changed. Thus, manually moving the microscope unit 3110 may sometimes be considered to be simple.

Meanwhile, in a case in which the microscopic operation system 3000 is applied to an ophthalmic surgery, an eye that is an operating site and the microscope unit 3110 are considered to have a substantially fixed positional relationship during the operation. That is, it is assumed that no major movement would be made once the microscope unit 3110 can be controlled to have a position and an attitude at which a desired eye-captured image is obtained. Therefore, the initial operation control and the trace operation control according to the first and second embodiments are considered to be well compatible with control over a position and an attitude of the microscope unit 3110 in an ophthalmic surgery in that the microscope unit 3110 is automatically moved so that the one designated position and attitude condition is satisfied.

In addition, it is assumed in the ophthalmic surgery that an image is photographed at a fairly high magnification factor to observe the eye that is a fairly small operating site. In the case in which photographing is performed with a high magnification factor, a captured image is significantly changed only by slightly changing a position and an attitude of the microscope unit 3110, and thus it is necessary to control the position and the attitude of the microscope unit 3110 with high precision, and manual manipulations are difficult in most cases. On the other hand, since a position and an attitude of the microscope unit 3110 can be automatically controlled in the initial operation control and the trace operation control according to the first and second embodiments, this system is particularly suitable for such a case in which photographing with a high magnification factor is required.

Furthermore, in the trace operation control according to the second embodiment, a position and an attitude of the microscope unit 3110 are automatically controlled so that the designated position and attitude condition is satisfied while movement of the operating site is traced. Meanwhile, in a operation such as a laparotomy other than ophthalmic surgeries, it is considered that a biological tissue that is an operating site is fairly large as described above and movement thereof during the operation is greater than in the ophthalmic surgeries, and thus if the microscope unit 3110 is moved tracing the movement of the biological tissue, the amount of movement of the microscope unit 3110 increases accordingly. On the other hand, since the eye is fairly small as an operating site and movement thereof during the operation is also small, even if the microscope unit 3110 is moved tracing the movement of the biological tissue, the amount of movement of the microscope unit 3110 is suppressed in a small range. Thus, safety can be secured even if the microscope unit 3110 is automatically moved.

Taking account of the above-described circumstances, the drive control systems 1 and 2 according to the first and second embodiments are considered to exhibit favorable effect when they are applied to ophthalmic surgeries.

Note that the term "corneal ring portion" used in the above description has substantially the same definition as terms "corneal boundary," "corneal range," and the like. In addition, for a term indicating a vertex direction, various terms that are generally used, such as "upward," "downward," "nose side," "ear side," and the like can be used. The various terms used in the above description can appropriately read as other terms that can be easily understood by a person skilled in the art.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control device including:

a control unit configured to control a position and an attitude of a microscope unit by driving an arm unit that supports the microscope unit on the basis of a captured image of an operating site photographed by the microscope unit during an operation so that a position and attitude condition set before the operation is satisfied, in which the position and attitude condition is a condition that prescribes a position and an attitude of the microscope unit with respect to the operating site to obtain a desired captured image corresponding to the position and attitude condition.

(2)

The control device according to (1), in which the position and attitude condition at least includes an instruction regarding an appearance of the image of the operating site.

(3)

The control device according to (2), in which the instruction regarding the appearance of the image of the operating site includes at least one of details of a position of the operating site in the captured image, details of a size of the operating site in the captured image, details of a shape of the operating site in the captured image, and details of a vertex direction in the captured image.

(4)

The control device according to any one of (1) to (3), in which the position and attitude condition includes at least one of an instruction regarding a photographing direction, an instruction regarding a magnification of the captured image, an instruction regarding a distance between the microscope unit and a floor, and an instruction regarding a distance between the microscope unit and the operating site.

(5)

The control device according to any one of (1) to (4), in which the operating site is an eye.

(6)

The control device according to (5), in which the position and attitude condition at least includes an instruction regarding an appearance of an image of the eye, and the instruction regarding the appearance of the image of the eye includes at least one of details of a position of a corneal ring part of the eye in the captured image, details of a size of the corneal ring part of the eye in the captured image, details of a shape of the corneal ring part of the eye in the captured image, and details of a vertex direction in the captured image.

(7)

The control device according to any one of (1) to (6), in which the position and attitude condition includes an instruction to maximize or minimize a specific index.

(8)

The control device according to (7), in which the operating site is an eye, the specific index is transillumination, and an instruction to maximize the transillumination includes that brightness of reflection light from a retina be at a maximum or that an eye axis of the eye and an optical axis of the microscope unit have a predetermined positional relationship.

(9)

The control device according to any one of (1) to (8), in which the position and the attitude of the microscope unit are controlled until the captured image photographed during the operation approximates the desired captured image corresponding to the position and attitude condition set before the operation.

(10)

The control device according to (9), in which whether the captured image photographed during the operation approximates the desired captured image corresponding to the position and attitude condition set before the operation is determined by comparing feature amounts extracted from the images.

(11)
The control device according to any one of (1) to (8), in which the position and the attitude of the microscope unit are controlled so that the position and attitude condition set before the operation is satisfied until an end instruction is input.

(12)
The control device according to any one of (1) to (11), in which the arm unit which supports the microscope unit is driven and the position and the attitude of the microscope unit are controlled so that the position and attitude condition is satisfied on the basis of a captured image overlooking a vicinity of the operating site including the operating site.

(13)
The control device according to any one of (1) to (12),
in which one position and attitude condition among position and attitude conditions that are registered in advance is set, and
the position and the attitude of the microscope unit are controlled so that the set position and attitude condition is satisfied.

(14)
The control device according to (13),
in which, in a case in which the position and the attitude of the microscope unit are modified after the position and the attitude of the microscope unit are controlled so that the set position and attitude condition is satisfied, registration details of the set position and attitude condition are updated on the basis of the modified position and attitude of the microscope unit.

(15)
The control device according to (13) or (14), in which the control unit causes an icon indicating the position and attitude condition that is registered in advance to be displayed on a display screen.

(16)
A control method including:
controlling, by a processor, a position and an attitude of a microscope unit by driving an arm unit that supports the microscope unit on the basis of a captured image of an operating site photographed by the microscope unit during an operation so that a position and attitude condition set before the operation is satisfied,
in which the position and attitude condition is a condition that prescribes a position and an attitude of the microscope unit with respect to the operating site to obtain a desired captured image corresponding to the position and attitude condition.

(17)
A microscope device for operation including:
a microscope unit configured to photograph a captured image of an operating site;
an arm unit configured to support the microscope unit; and
a control device configured to control a position and an attitude of the microscope unit by driving the arm unit on the basis of a captured image of the operating site photographed by the microscope unit during an operation so that a position and attitude condition set before the operation is satisfied,
in which the position and attitude condition is a condition that prescribes a position and an attitude of the microscope unit with respect to the operating site to obtain a desired captured image corresponding to the position and attitude condition.

(16)
A control method including controlling, by a processor, a position and an attitude of a microscope unit by driving an arm unit that supports the microscope unit on the basis of a captured image of an operating site photographed by the microscope unit during an operation so that a position and attitude condition set before the operation that is a condition that prescribes a position and an attitude of the microscope unit with respect to the operating site to obtain a desired captured image is satisfied.

(17)
A microscope device for operation including:
a microscope unit configured to photograph a captured image of an operating site;
an arm unit configured to support the microscope unit; and
a control device configured to control a position and an attitude of the microscope unit by driving the arm unit on the basis of a captured image of the operating site photographed by the microscope unit during an operation so that a position and attitude condition set before the operation that is a condition that prescribes a position and an attitude of the microscope unit with respect to the operating site to obtain a desired captured image is satisfied.

REFERENCE SIGNS LIST 1, 2 drive control system
110 pre-operation information acquisition unit
120 in-operation information acquisition unit
130 driving unit
140, 150 control unit
141 position and attitude condition setting unit
142 state recognition unit
143 state comparison unit
144 drive control unit
153 end determination unit
3000 microscopic operation system
3100 microscope device
3110 microscope unit
3120 arm unit
3121a first joint unit
3121b second joint unit
3121c third joint unit
3121d fourth joint unit
3121e fifth joint unit
3121f sixth joint unit
3123a first ring
3123b second ring
3123d third ring
3123d fourth ring
3123e fifth ring
3123f sixth ring
3130 base unit
3200 control device
3300 display device

The invention claimed is:
1. A surgical imaging system comprising:
a memory configured to store a plurality of position and attitude conditions each corresponding to a fixed position and attitude of a microscope;
display circuitry configured to cause a plurality of images to be displayed simultaneously, each of the plurality of images corresponding to a different position and attitude condition in the plurality of position and attitude conditions;

input circuitry configured to receive a user input operation to select, from the displayed plurality of images, a first displayed image corresponding to a first position and attitude condition in the plurality of stored position and attitude conditions and corresponding to a first fixed position and attitude of the microscope to capture a first image of a surgical site by the microscope;

an arm configured to support the microscope and adjust a position and attitude of the microscope to be a second fixed position and attitude that is different than the first fixed position and attitude;

the microscope configured to capture a second image of the surgical site from the second fixed position and attitude; and processing circuitry configured to control, in response to the user input operation, a position and an attitude of the microscope to be changed from the second fixed position and attitude to the first fixed position and attitude by driving the arm based on the stored fir position and attitude condition so that a third image of the surgical site, captured by the microscope, corresponds to the first image.

2. The surgical imaging system according to claim 1, wherein the first position and attitude condition is stored in association with a user of the microscope.

3. The surgical imaging system according to claim 1, wherein the first position and attitude condition is stored in association with a kind of surgical procedure.

4. The surgical imaging system according to claim 1, wherein the processing circuitry is configured to drive the arm so that an optical axis of the microscope stays pointed at a certain point in space.

5. The surgical imaging system according to claim 1, wherein the microscope includes an imaging device configured to generate an image signal corresponding to stereoscopic vision.

6. The surgical imaging system according to claim 1, wherein the microscope includes an imaging device having an auto-focus (AF) function.

7. The surgical imaging system according to claim 1, further comprising a display device configured to display the third image of the surgical site captured by the microscope.

8. The surgical imaging system according to claim 1, wherein the first position and attitude condition includes an instruction regarding an appearance of the first image of the surgical site.

9. The surgical imaging system according to claim 8, wherein the instruction regarding the appearance of the first image of the surgical site includes at least one of: details of a position of the surgical site in the first image, details of a size of the surgical site in the first image, details of a shape of the surgical site in the first image, and details of a vertex direction in the first image.

10. The surgical imaging system according to claim 1, wherein the first position and attitude condition includes at least one of: an instruction regarding an image capturing direction, an instruction regarding a magnification of the first image, an instruction regarding a distance between the microscope and a floor, and an instruction regarding a distance between the microscope and the surgical site.

11. The surgical imaging system according to claim 1, wherein the surgical site is an eye.

12. The surgical imaging system according to claim 11, wherein the first position and attitude condition includes an instruction regarding an appearance of the first image of the eye, and the instruction regarding the appearance of the first image of the eye includes at least one of: details of a position of a corneal ring part of the eye in the first image, details of a size of the corneal ring part of the eye in the first image, details of a shape of the corneal ring part of the eye in the first image, and details of a vertex direction in the first image.

13. The surgical imaging system according to claim 1, wherein the first position and attitude condition includes an instruction to maximize or minimize an index.

14. The surgical imaging system according to claim 13, wherein the surgical site is an eye, the index is transillumination, and an instruction to maximize the transillumination includes that brightness of reflection light from a retina be at a maximum or that an eye axis of the eye and an optical axis of the microscope have a predetermined positional relationship.

15. The surgical imaging system according to claim 1, wherein the position and the attitude of the microscope are controlled until the third image captured during a surgical operation sufficiently corresponds to the first image corresponding to the first position and attitude condition set before the surgical operation.

16. The surgical imaging system according to claim 15, wherein whether the third image captured during the surgical operation sufficiently corresponds to the first image, corresponding to the position and attitude condition set before the surgical operation, is determined by comparing feature amounts extracted from the first and third images.

17. The surgical imaging system according to claim 1, wherein the position and the attitude of the microscope are controlled so that the first position and attitude condition set before a surgical operation is satisfied until an end instruction is input.

18. The surgical imaging system according to claim 1, wherein the arm which supports the microscope is driven and the position and the attitude of the microscope are controlled so that the first position and attitude condition is satisfied on the basis of a fourth image overlooking a vicinity of the surgical site and includes the surgical site.

19. The surgical imaging system according to claim 1, wherein one position and attitude condition, among the plurality of position and attitude conditions that are registered in advance, is pre-set, and the processing circuitry is further configured to control the position and the attitude of the microscope so that the one position and attitude condition is satisfied.

20. The surgical imaging system according to claim 19, wherein, in a case that the position and the attitude of the microscope are modified after the position and the attitude of the microscope were controlled by the processing circuitry so that the first position and attitude condition was satisfied, registration details of the one position and attitude condition are updated on the basis of the modified position and attitude of the microscope.

21. The surgical imaging system according to claim 19, wherein the plurality of images are displayed on a display screen.

22. A method comprising:

storing a plurality of position and attitude conditions, each corresponding to a fixed position and attitude of a microscope;

displaying simultaneously a plurality of images, each corresponding to a different position and attitude condition in the plurality of position and attitude conditions;

receiving a user input operation to select, from the displayed plurality of images, a first displayed image corresponding to a first position and attitude condition in the plurality of stored position and attitude conditions and corresponding to a first fixed position and attitude of the microscope to capture a first image of a surgical site by the microscope, in a memory;

adjusting a position and attitude of the microscope to be a second fixed position and attitude that is different than the first fixed position and attitude;

capturing a second image of the surgical site with the microscope supported by an arm from the second fixed position and attitude; and controlling, using processing circuitry and in response to the user input operation, a position and an attitude of the microscope to be changed from the second fixed position and attitude to the first fixed position and attitude by driving the arm based on the stored first position and attitude condition so that a third image of the surgical site, captured by the microscope, corresponds to the first image.

23. An apparatus comprising:

processing circuitry configured to control, in response to a user input operation received by input circuitry, a position and an attitude of a microscope configured to capture a third image of a surgical site by driving an arm configured to support the microscope from a second fixed position and attitude of the microscope where a second image is captured, based on a first position and attitude condition stored in a memory and corresponding to a first fixed position and attitude of the microscope used to capture a first image of the surgical site by the microscope, the first position and attitude condition being selected from a plurality of position and attitude conditions stored in the memory by input circuitry that selects a first displayed image corresponding to the first position and attitude condition from a plurality of simultaneously displayed images, so that the third image of the surgical site, captured by the microscope, corresponds to the first image, and wherein the second fixed position and attitude of the microscope is different from the first fixed position and attitude of the microscope.

24. The surgical imaging system according to claim 1, wherein each of the stored plurality of position and attitude conditions further includes focus and magnification information corresponding to the first fixed position and attitude of the microscope to capture the first image of the surgical site by the microscope, and the processing circuitry is further configured to control, in response to the user input operation, a focus and magnification of the microscope to capture the third image, based on the stored first condition information.

25. The surgical imaging system according to claim 1, wherein each of the stored plurality of position and attitude conditions further includes distance information between the microscope and the surgical site corresponding to the first fixed position and attitude of the microscope to capture the first image of the surgical site by the microscope, and the processing circuitry is further configured to control, in response to the user input operation, the focus and magnification of the microscope to capture the third image, based on the stored first condition information.

26. The surgical imaging system according to claim 1, wherein each of the stored plurality of position and attitude conditions further includes instruction information corresponding to the first fixed position and attitude of the microscope to capture the first image of the surgical site by the microscope, the instruction information indicating whether to maximize a brightness of reflection light from a portion of the surgical site, and the processing circuitry is further configured to control, in response to the user input operation, execution of the instruction information in the stored first condition information to capture the third image.

27. The surgical imaging system according to claim 1, wherein each of the plurality of images to be displayed includes an icon.

* * * * *